(12) United States Patent
Exley

(10) Patent No.: US 8,853,222 B2
(45) Date of Patent: Oct. 7, 2014

(54) TREATMENT OF HERPES VIRUS RELATED DISEASES

(76) Inventor: Ray W. Exley, Beverly Hills, CA (US)

( * ) Notice: Subject to any disclaimer, the term of this patent is extended or adjusted under 35 U.S.C. 154(b) by 390 days.

(21) Appl. No.: 12/921,006

(22) PCT Filed: Mar. 6, 2009

(86) PCT No.: PCT/US2009/036393
§ 371 (c)(1),
(2), (4) Date: Jan. 24, 2011

(87) PCT Pub. No.: WO2009/111739
PCT Pub. Date: Sep. 11, 2009

(65) Prior Publication Data
US 2011/0112117 A1 May 12, 2011

Related U.S. Application Data

(60) Provisional application No. 61/034,804, filed on Mar. 7, 2008, provisional application No. 61/050,564, filed on May 5, 2008.

(51) Int. Cl.
*A61K 31/52* (2006.01)
*A61K 45/06* (2006.01)
*A61K 31/522* (2006.01)
*A61K 31/195* (2006.01)

(52) U.S. Cl.
CPC .............. *A61K 31/522* (2013.01); *A61K 45/06* (2013.01); *A61K 31/52* (2013.01); *A61K 31/195* (2013.01)
USPC ..................... 514/263.1; 514/263.3

(58) Field of Classification Search
CPC ...................................... A61K 31/52
USPC ........................... 514/263.1, 263.3
See application file for complete search history.

(56) References Cited

U.S. PATENT DOCUMENTS 5,543,414 A * 8/1996 Nestor et al. ............. 514/263.38

* cited by examiner

*Primary Examiner* — Renee Claytor
(74) *Attorney, Agent, or Firm* — Tom M. Moran

(57) ABSTRACT

Anti-herpetic material such as 2-aminopurine derivatives, e.g., the aminocyclopropylcarboxylate derivatives of acyclovir, penciclovir, and ganciclovir, are described to prevent or treat autoimmune disease or a disease originating from an abnormal functioning of the sympathetic chain in a human subject. Prolonged use of the anti-herpetic compounds reduces prodrome, vesicle formation and viral shedding. The anti-herpetic compounds may be administered alone or in combination with a compound that reduces the rate of renal excretion of the anti-herpetic compound. The anti-herpetic compounds are particularly useful when administered at a level equivalent in activity to at—least about 150 mg/kg famciclovir per day.

5 Claims, No Drawings

TREATMENT OF HERPES VIRUS RELATED DISEASES

CROSS-REFERENCE TO RELATED APPLICATIONS

This application claims priority to provisional applications U.S. Ser. No. 61/034,804, filed on 7 Mar. 2008, and 61/050,564, filed on 5 May 2008, each of which is incorporated herein by reference in its entirety.

BACKGROUND OF THE INVENTION

1. Field of the Invention

The present invention relates to the use of certain derivatives of acyclovir, penciclovir and ganciclovir, and other antiherpetic compounds to prevent prodrome and vesicle outbreaks in a human subject having a herpes virus infection, particularly HSV-II. The use also prevents viral shedding. The invention further relates to the use of the derivatives to treat diseases originating from the abnormal functioning of the sympathetic nervous chain, particularly those that express as conditions associated with autoimmune disease. A representative compound is the 1-aminocyclopropanecarboxylate ester of acyclovir; another is the corresponding ester of penciclovir. The derivatives may be administered alone or in combination with a compound, such as probenecid, that reduces the rate of renal excretion of the derivative.

2. State of the Art

It is known in the prior literature that certain compounds are useful for treating viruses in the herpes simplex family, e.g., herpes simplex virus-type II ("HSV-II") and herpes zoster virus ("HZV"). These compounds include acyclovir (2-amino-1,9-dihydro-9-[(2-hydroxyethoxy)methyl]-6H-purin-6-one); valacyclovir (L-valine, 2-[(2-amino-1,6-dihydro-6-oxo-9H-purin-9-yl)methoxy]ethyl ester); famciclovir (2-[2-(2-amino-9H-purin-9-yl)ethyl]-1,3-propanediol diacetate); penciclovir (9-[4-hydroxy-3-(hydroxymethyl)butyl]guanine); ganciclovir (9-[[2-hydroxy-1-(hydroxymethyl)ethoxy]methyl]guanine); the L-valyl ester of ganciclovir, and others. See U.S. Pat. No. 4,199,574 to Schaeffer issued 22 Apr. 1980; U.S. Pat. No. 4,355,032 to Verheyden and Martin issued 19 Oct. 1982; U.S. Pat. No. 4,957,924 to Beauchamp, L. issued 18 Sep. 1990; U.S. Pat. No. 5,059,604 to Krenitsky, et al. issued 22 Oct. 1991; U.S. Pat. No. 5,246,937 to Hamden, et al. issued 21 Sep. 1993; U.S. Pat. No. 5,250,688 to Hamden, et al. issued 5 Oct. 1993; and U.S. Pat. No. 5,075,445 to Jarvest, et al. issued 24 Dec. 1991.

The Food and Drug Administration (FDA) currently approves acyclovir and penciclovir for the treatment of vesicle outbreaks of HSV-I, HSV-II, herpes zoster (shingles), and varicella (chickenpox). Famciclovir (a pro-drug for penciclovir) is FDA approved for the treatment of the vesicle outbreak phase of herpes zoster and genital herpes (HSV-II). Such treatment requires blood levels between 0.5 microgram/milliliter (µg/mL) and 1.0 µg/mL for acyclovir and similar levels for penciclovir. The currently recognized oral doses required to reach this blood level for an adequate amount of time (which varies according to the virus being treated and is based upon the effective half-life of the drug) for reasonable therapeutic effect are as follows:

1. FAMVIR brand famciclovir is approved for use against herpes Zoster at the oral doses of up to 500 mg three times per day for a 100 kg person or about 1.5 g, and against HSV-II at doses of 125 mg t.i.d. up to 250 mg t.i.d. for suppression of recurrent genital herpes. The absorption is linear in this dose range.

2. ZOVIRAX brand acyclovir is approved for several different uses against several different presentations of herpes viruses at oral doses that range between 200 mg three times per day and 800 mg per 100 kg 5 times per day. This would amount to a high dose of 4 g per day for a 100 kg subject. Because the absorption of acyclovir is non-linear in this dose range GlaxoSmithKline, the manufacturer, has discouraged the use of higher doses because it believes little more can be absorbed with doses higher than the maximum dose of 800 mg 5 times per day, which in most patients gives a blood level of about 1.61 µg/mL.

3. DENAVIR brand of penciclovir cream is approved for the treatment of herpes labialis (cold sores or HSV-I).

4. VALTREX brand of valacyclovir is approved for the treatment of herpes zoster, genital herpes, and herpes labialis in certain conditions.

5. CYTOVENE brand of ganciclovir is approved for the treatment of Cytomegalovirus (CMV) retinitis, and prevention of CMV disease in patients with HIV infection and in certain organ transplant recipients.

6. VALCYTE brand of valganciclovir is approved for the treatment of Cytomegalovirus (CMV) retinitis, and prevention of CMV disease in heart, kidney and kidney-pancreas transplantations.

U.S. Pat. No. 5,559,114 ("the '114 patent") and International Application No. PCT/US95/16207 ("the 16207 application") teach that the administration to patients with autoimmune disease of high doses (about 8 times the recommended dose) of the above mentioned anti-viral drugs results in improvement in the patient's condition.

International Publication WO 2006/127217 A2 describes both the synthesis and utility of cyclopropanecarboxylate esters of acyclovir as medicaments with antiviral activity. Disclosed is the preferred aminocyclopropanecarboxylate ester that shows enhanced stability to hydrolytic conditions at both acidic and neutral pH compared to valacyclovir.

SUMMARY OF THE INVENTION

One aspect of this invention is a method for treating or preventing a disease or condition originating from an abnormal functioning of the sympathetic nervous system ("SNS") in a human subject. This method of treatment comprises administering on a daily basis to the subject in need thereof a therapeutically effective amount of a compound represented by Formulas (I) or (II) below, or pharmaceutically acceptable salt thereof, for a period of time sufficient to alleviate the subject's signs or symptoms associated with the disease, wherein the therapeutically effective amount of the compound is equivalent in activity to at least about 150 mg famciclovir per kg body weight of the subject per day. The method is particularly useful in a subject that is infected with a herpes virus, such as HSV-II, with famciclovir being the compound.

Another aspect of this invention is a method for treatment of a subject exhibiting the signs or symptoms of a herpes viral disease that include chronic pain, failure of muscles to relax, sudden muscle spasm, severe fatigue, or a loss of control of or sensation in autonomic muscle. The method comprises choosing a compound of Formulas (I) or (II), or pharmaceutically acceptable salt thereof, that is equivalent in activity against the herpes virus causative of the viral disease to at least 150 mg famciclovir per kg body weight of the subject per day, calculating the amount of the compound needed as therapeutically effective for the subject, administering the compound at the amount calculated for a period of time sufficient to alleviate the signs or symptoms in the subject, and continuing the administration of the compound to the subject at the calculated amount. Optionally, and preferably, the subject is first tested for the presence of a herpes virus, such as HSV-II, and if positive, the other steps are undertaken.

Another aspect of the invention is a system for treating a human subject having a disease originating from abnormal functioning of the subject's SNS, which system comprises (a) a container holding a pharmaceutical composition comprising a pharmaceutically acceptable excipient and a compound represented by Formulas (I) or (II), or pharmaceutically acceptable salt thereof, and (b) instructions associated with the container for administering the pharmaceutical composition to the subject at a therapeutically effective amount equivalent in activity to at least about 150 mg famciclovir per kg body weight of the subject per day. The pharmaceutical composition utilized in this system would be in the form of a powder or granules that is reconstitutable with water, or alternatively could be administered as a suppository. The rate of administration of the pharmaceutical composition to the subject could be four times a day every six hours.

Another aspect of the invention is the use of a compound of Formulas (I) or (II), or pharmaceutically acceptable salt thereof, in the preparation of a composition for treating a human subject for a disease originating from the abnormal functioning of the SNS, wherein the composition is administered to the subject at an amount equivalent to the activity in the subject of at least about 150 mg famciclovir per kg body weight of the subject per day. The pharmaceutical composition utilized in this use would be in the form of a powder or granules that is reconstitutable with water, or alternatively could be administered as a suppository. The rate of administration of the pharmaceutical composition to the subject could be four times a day every six hours.

Another aspect of the invention is a method for treating or preventing a disease in a human subject having signs or symptoms of a disease originating from an abnormal functioning of the SNS, who is further infected with a herpes simplex viral infection. The method comprises (a) identifying a subject having a sign or symptom of a disease originating from an abnormal functioning of the SNS, (b) testing the subject for the presence of a herpes simplex virus, and (c) if the result of the test is positive, administering on a daily basis to the subject a therapeutically effective amount of a compound represented by Formulas (I) or (II), or pharmaceutically acceptable salt thereof, for a period of time sufficient to alleviate a sign or symptom of the subject associated with the disease, wherein the therapeutically effective amount of the compound is equivalent in activity to at least about 150 mg famciclovir per kg body weight of the subject per day. The rate of administration of the pharmaceutical composition to the subject could be four times a day every six hours.

Another aspect of the invention is a method for improving reduced renal function as measured by creatinine clearance in a human subject having a herpes virus infection, which method comprises administering on a daily basis to the subject a therapeutically effective amount of a compound of Formulas (I) or (II), or pharmaceutically acceptable salt thereof, for a period of time sufficient to increase the rate of creatinine clearance in the subject, wherein the therapeutically effective amount of the compound is equivalent in activity to at least about 150 mg famciclovir per kg body weight of the subject per day. The rate of administration of the pharmaceutical composition to the subject could be four times a day every six hours.

Another aspect of the invention is a powder or granular composition for treating a human subject having a disease originating from abnormal functioning of the subject's SNS and further being infected with a herpes virus, which composition comprises (a) a compound represented by Formulas (I) or (II), or pharmaceutically acceptable salt thereof, and (b) a pharmaceutically-acceptable excipient that aids in dissolving or suspending the compound of (a) in water so that the pharmaceutical composition may be administered to the subject at a therapeutically effective amount equivalent in activity to at least about 150 mg famciclovir per kg body weight of the subject per day.

Another aspect of the invention is a liquid composition for treating a human subject having a disease originating from abnormal functioning of the subject's SNS, which composition comprises (a) a compound represented by Formulas (I) or (II), or pharmaceutically acceptable salt thereof, and (b) a liquid pharmaceutically-acceptable excipient that aids in dissolving or suspending the compound of (a) so that the pharmaceutical composition may be administered to the subject at a therapeutically effective amount equivalent in activity to at least about 150 mg famciclovir per kg body weight of the subject per day.

Another aspect of this invention is a composition for treating a human subject having a disease originating from abnormal functioning of the subject's SNS, particularly where the subject is infected with a herpes virus, which composition comprises (a) a compound represented by Formulas (I) or (II), or pharmaceutically acceptable salt thereof, (b) a compound that decreases the rate of renal excretion of the compound of (a), and (c) a pharmaceutically-acceptable excipient. The pharmaceutical composition utilized in this composition would be in the form of a powder or granules that is reconstitutable with water, or alternatively could be administered as a suppository.

Another aspect of this invention is a method for preventing prodrome and vesicle outbreaks in a human subject having a herpes virus infection, which method comprises administering on a daily basis to the subject a compound represented by Formulas (I) or (II), or pharmaceutically acceptable salt thereof, wherein the daily dose of the compound is equivalent in its effect on the subject to at least about 150 mg famciclovir per kg body weight of the subject per day.

Another aspect of this invention is a method of preventing prodrome and vesicle outbreaks in a human subject having a herpes virus infection, which method comprises administering to the subject an antiviral compound of Formulas (I) or (II), or pharmaceutically acceptable salt thereof, effective against herpes viruses at a dose regimen sufficient to achieve ongoing relief of signs or symptoms associated with the herpes infection.

Another aspect of the invention is a system for preventing prodrome and vesicle outbreaks in a human subject, which system comprises a container holding a composition comprising a compound represented by Formulas (I) or (II), or pharmaceutically acceptable salt thereof, and a pharmaceutically acceptable excipient, wherein the container is associated with instructions for administering the composition to the subject at a daily dose of the compound that is equivalent to at least about 150 mg famciclovir per kg body weight of the subject per day on an ongoing basis to reduce the prodrome and vesicle outbreaks.

Another aspect of the invention is a method for reducing viral shedding in a human subject having a herpes virus infection, which method comprises administering on a daily basis to the subject a compound represented by Formulas (I) or (II), or pharmaceutically acceptable salt thereof, wherein the daily dose of the compound is equivalent in its effect on the subject to at least about 150 mg famciclovir per kg body weight of the subject per day.

Another aspect of the invention is a method of reducing viral shedding in a human subject having a herpes virus infection, which method comprises administering to the subject an antiviral compound effective against herpes viruses at a dose regimen sufficient to achieve ongoing reduction of viral shedding associated with the herpes infection. Preferably, the viral shedding is reduced to level that is below 10% of the rate of viral shedding in the subject in the absence of administration of the compound to the subject.

Another aspect of the invention is a system for reducing viral shedding in a human subject, which system comprises a container holding a composition comprising a compound represented by Formulas (I) or (II), or pharmaceutically acceptable salt thereof, and a pharmaceutically acceptable excipient, wherein the container is associated with instructions for administering the composition to the subject at a daily dose of the compound that is equivalent to at least about 150 mg famciclovir per kg body weight of the subject per day on an ongoing basis to reduce viral shedding.

Another aspect of this invention is a method for improving renal function as measured by creatinine clearance in a human subject having a disease originating from abnormal functioning of the subject's SNS, which method comprises administering on a daily basis to the subject a therapeutically effective amount of a compound represented by Formulas (I) or (II), or pharmaceutically acceptable salt thereof, for a period of time sufficient to increase the rate of creatinine clearance in the subject, wherein the therapeutically effective amount of the compound is equivalent in activity to at least about 150 mg famciclovir per kg body weight of the subject per day.

Another aspect of this invention is a powder or granular composition for treating a human subject having an herpes virus infection, such as herpes simplex virus II, which composition comprises (a) a compound represented by Formulas (I) or (II), or pharmaceutically acceptable salt thereof, and (b) a pharmaceutically-acceptable excipient that aids in dissolving or suspending the compound of (a) in water so that the pharmaceutical composition may be administered to the subject at a therapeutically effective amount equivalent in activity to at least about 150 mg famciclovir per kg body weight of the subject per day.

Another aspect of this invention is a liquid composition for treating a human subject having an herpes virus infection, such as herpes simplex virus II, which composition comprises (a) a compound represented by Formulas (I) or (II), or pharmaceutically acceptable salt thereof, and (b) a liquid pharmaceutically-acceptable excipient that aids in dissolving or suspending the compound of (a) so that the pharmaceutical composition may be administered to the subject at a therapeutically effective amount equivalent in activity to at least about 150 mg famciclovir per kg body weight of the subject per day.

Another aspect of this invention is a composition for treating a human subject having an herpes virus infection, such as herpes simplex virus II, which composition comprises (a) a compound represented by Formulas (I) or (II), or pharmaceutically acceptable salt thereof, (b) a compound that decreases the rate of renal excretion of the compound of (a); and (c) a pharmaceutically-acceptable excipient. Preferably, the w/w ratio of compound (a) to compound (b) is about 25:1 to about 50:1.

Another aspect of this invention is a method of treating a subject having a herpes simplex, herpes zoster, cytomegalovirus or herpes simplex keratitis infection that comprises administering an effective amount of a compound of Formulas (I) or (II), or pharmaceutically acceptable salt thereof, to a subject in need thereof.

The present invention also provides for the use of a compound of Formulas (I) or (II), or pharmaceutically acceptable salt thereof, as a medicament. The present invention also provides for the use of the compound of Formulas (I) or (II), or pharmaceutically acceptable salt thereof, for the manufacture of a medicament for treating a herpes virus infection in a subject having such an infection.

For each of the various aspects of the invention, Formula (I) is

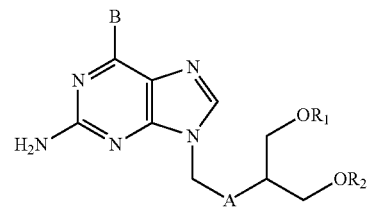

wherein A is $CH_2$ or O; B is H, Cl, alkoxy of 1-6 carbon atoms, phenoxy, phenylalkoxy where alkoxy is 1-6 carbon atoms, $NH_2$, OH or SH; $R_1$ is independently $C(O)CH(NH_2)R_4$, proline, hydroxyproline, or

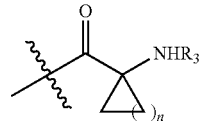

wherein $R_4$ is H or alkyl of 1-4 carbon atoms, n is 1-4 and $R_3$ is H or alkyl of 1-4 carbon atoms; $R_2$ is independently H, $C(O)R_5$ where $R_5$ is alkyl of 1-5 carbon atoms, $C(O)CH(NH_2)R_4$, proline, hydroxyproline, or

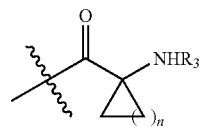

wherein n, $R_3$ and $R_4$ are as defined.

In a preferred embodiment, the group $—C(O)CH(NH_2)R_4$ is derived from an L-amino acid.

Formula (II) is

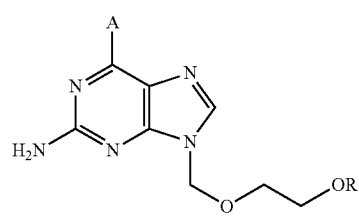

wherein A is OH and R is

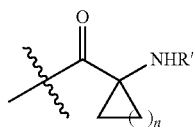

wherein n is 1-4, and R' is H or alkyl of 1-4 carbon atoms.

For each of the aspects of the invention the compound of Formulas (I) or (II) may be administered alone, or as a pharmaceutically acceptable salt, or in combination with a compound that decreases the rate of renal excretion of the anti-herpetic drug. An example of such a compound is probenecid (4-(dipropylsulfamoyl)benzoic acid).

Other aspects of the invention may be apparent to one of ordinary skill in the art upon reading the following specification and claims.

DETAILED DESCRIPTION OF THE INVENTION

This invention is based in part on the inventor's discovery that certain 2-amino purine derivatives are useful for treating a broad range of diseases or conditions previously not adequately treated by any known means. Prior to the inventor's discovery, the cause of these diseases was and is unknown in the general medical knowledge. While not wishing to be bound by any particular theory or explanation of why the invention works in its various aspects, the mechanism of causation proposed in this application is linked in part to the activity of one or more herpes viruses in the body, and the body's response to that virus, particularly the immune system response and changes in the activity of various nerves, particularly the sympathetic nerve chain. The current state of knowledge before the work described in this application has resulted in many of these conditions having many different names, and most occur as or associated with "autoimmune" diseases, which in current knowledge means the cause is unknown. Such conditions include those with particularly severe chronic pain including fibromyalgia or irritable bowel syndrome, and many other diseases and conditions referred to by other names discussed hereinafter, including tissue damage and organ failure. Based on evidence available, the inventor believes that the cause of all of these diseases is the direct effect of the virus and the body's response to the presence of a herpes virus, particularly HSV-II, genital herpes. One effect of the virus is to alter the rate of firing of the SNS. The diseases are theorized to be caused by the abnormal functioning of the SNS, usually the excessive firing of the sympathetic cells, which is caused by herpes virus living and reproducing in the cells of the sympathetic chain. HSV-II also can cause diminished or stopped firing of the cells, shutting down some functions and sensations. HSV-II prefers the cells of the sympathetic chain, which it will inhabit first after a human acquires this virus. Later it may infect other cells of the nervous system including the meninges and brain tissue (e.g.: aseptic, autoimmune meningio-encephalitis).

This invention is based in part on the observations by the inventor that certain prior approaches to the treatment of autoimmune disease using ongoing high levels of anti-herpes drugs were useful to suppress autoimmune disease signs or symptoms to a certain extent, but that those levels seemed to have little or no effect on long term suppression of vesicle formation, prodrome occurrence, or viral shedding. The inventor now proposes a method of treatment and a product that results in long term suppression of herpes virus vesicle formation, prodrome occurrence, and viral shedding in a subject having a herpes virus infection such as HSV-II.

The compounds that are useful in the process, system, and composition of this invention are shown as Formulas (I) or (II), as discussed herein. The inventor recognized that the compounds of Formulas (I) or (II) may offer certain advantages over other compounds known in the art for treating conditions discussed herein. For example, FAMVIR®, DENAVIR®, ZOVIRAX®, and VALTREX® are all anti-herpetic products sold for the suppression of HSV-I, HSV-II, or HZV vesicles. The dose for each of these products is relatively low, for the FDA-approved uses. The '114 patent and the 16207 application taught that high doses (about 8 to 12 times recommended dose, depending on the compound) of the marketed products are useful for treating conditions associated with autoimmune diseases. Further work by the inventor of the instant invention resulted in discovery that even higher oral doses of the marketed products such as FAMVIR, ZOVIRAX, or VALTREX are useful in treating diseases originating from an abnormal functioning of the sympathetic nervous chain (including conditions associated with autoimmune disease) and for preventing herpes prodrome and vesicle outbreaks, along with viral shedding. Such compounds can be administered alone or in combination with a compound such as probenecid that reduces the rate of renal excretion of the anti-herpetic compound. These concepts are set forth in the provisional U.S. patent applications 60/989,789, 60/989,792, 60/989,793 and 60/989,794, all filed on 21 Nov. 2007, and all of which are incorporated herein by reference. Those applications were combined as PCT application No. PCT/US2008/084246, filed on 20 Nov. 2008, which is also incorporated herein by reference. In all cases, the treatment relies primarily on the oral administration of high doses of a known anti-herpetic compound, preferably requiring that a patient takes multiple large tablets or capsules four times daily.

The inventor of the instant application recognizes that a problem may exist with a large segment of the patient population that might have trouble swallowing multiple tablets or capsules throughout the day. The inventor recognized a solution to the problem by proposing to use a compound that would require a smaller amount of the active compound to achieve the same results compared to using the compounds previously used. Such a compound would have, i.a., enhanced stability to hydrolytic conditions at both acidic and neutral pH, allowing the compound to remain in the stomach and blood longer before being converted to a biologically active form to treat a patient in need of treatment.

Compounds useful in this invention are shown in Formulas (I) and (II). The compounds are precursors of acyclovir, penciclovir, ganciclovir or others, and are administered in doses equivalent in activity to a standard famciclovir (FAMVIR-Novartis, generic version from Teva Pharmaceuticals) as taught in the provisional and PCT applications mentioned above. Famciclovir converts to penciclovir after being administered to a patient. The amount of famciclovir may range from 150 mg/kg/day to 400 mg/kg/day, or more. A compound of Formulas (I) or (II), or pharmaceutically acceptable salt thereof, will have an activity equivalent to famciclovir to achieve the results, as can be determined by one of ordinary skill in the art once presented with this patent application.

Diseases Originating from Abnormal Functioning of the SNS

In one aspect, a disease treated in accordance with this invention usually is caused by decreased blood flow to the affected tissue or organ, which in turn is caused by over-contraction of the small blood vessels supplying the tissue or organ. The over-contraction is caused by "hypertonus" of the muscles of the walls of the small blood vessels. The hypertonus is caused by the over activity of the sympathetic cells that control the tension or tonus of the resting muscle cells. The sympathetic chain over activity is caused by the virus reproduction inside the cells of the sympathetic chain.

This treatment of this aspect of the invention is thought to be effective because treatment restores the sympathetic nerves to a more normal state by suppressing the virus, which lowers or eliminates the abnormal firing of the sympathetic nerves thus leading to proper tonus of the muscle cells that affect the proper blood flow in the tissue or organ affected. The resulting restored normal blood flow reduces inflammation, scarring, destruction, and pain that was caused by the abnormal sympathetic chain activity and altered blood flow, secondary to the virus reproducing in the cells of the sympathetic chain. This treatment suppresses the herpes virus reproduction and returns the sympathetic chain, blood flow and the tissue or organ back to nearly normal functioning. Also, nervous system functions previously shut down, presumably by the virus activity, recover both motor and sensory functions.

The inventor's new theory of causation leads to this new treatment for these (autoimmune) diseases and other related conditions. This treatment is much more effective with fewer serious side effects than prior treatments that were only intended to suppress the immune system, but do nothing to suppress the causative agent, the virus. That was because prior to this inventor's work, the cause of all of these diseases, including "autoimmune diseases", and related conditions was unknown. The inventor recognized that the compounds of Formulas (I) and (II), or pharmaceutically acceptable salt thereof, should have little effect in the human body but to suppress virus thymidine kinase, and thus be useful to treat one or more of the herpetic viruses, particularly HSV-II, thought by the inventor to cause these conditions. This treatment has few serious side effects, and none of the side effects of previous treatments based on other theories of causation, or no theory of causation.

This treatment with compounds of Formulas (I) or (II), or pharmaceutically acceptable salt thereof, has not been previously described because the manufacturers of currently approved anti-viral drug products (e.g., ZOVIRAX) imply that very high doses, which are needed to suppress the virus, would be renal toxic. The inventor is not aware of any studies that were performed that demonstrated renal damage at the currently recommend or higher dose levels. The warning is based apparently solely upon the observation that drug crystals were observed in the kidneys of sacrificed animals after they received doses higher than currently recommended by the manufacturer of an FDA-approved product, but much lower than the doses taught in this application. This finding of crystals was apparently extrapolated by the manufacturer to mean that kidney damage would occur from the crystals. The compounds of Formulas (I) or (II), or pharmaceutically acceptable salt thereof, appear to be well-suited for administration to patients at high levels compared to those used to suppress herpes vesicle outbreaks, but at dosage levels lower than this for acyclovir, valacyclovir, or famciclovir, particularly if the anti-herpetic is co-administered with a compound that reduces the rate of renal excretion, e.g., probenecid.

As mentioned above, the '114 patent and the '16207 application teach that administration of high levels of certain 2-amino purine derivatives to patients with autoimmune disease results in certain improvements in the patients' condition. However, the inventor discovered that while the previous treatment resulted in amelioration of certain signs or symptoms to allow a patient to function in a more normal fashion, the autoimmune disease can be still be debilitating, with only moderate recovery of organ function and continued (though reduced) chronic pain. Subjectively a patient felt noticeably better as a result of the previous treatment, even to the extent of thinking 80 or 90% of the symptoms were relieved, but clearly additional relief was appropriate as time went on. Other symptoms present, such as unpredictable diarrhea and ongoing occasional severe pain. As pointed out above, the discovery of the effectiveness of the use of extraordinarily high doses of certain anti-viral compounds has led to an entirely new theory of the causes and mechanisms of a wide range of diseases and to successful, ongoing methods and systems of treatment of the newly identified organization of a family of diseases, as discussed in greater detail hereinafter.

In the human body organic and inorganic molecules interact to form organelles and other material to form cells, which in turn combine to form tissue with special functions. Generally these are classified as epithelium tissues, connective tissues, muscle tissue, and neural tissue. Some of these tissues can combine to form organs with various functions that then interact in organ systems. A discussion of these systems and their organization can be found in the tenth edition of "Principles of Anatomy and Physiology" by Tortora and Grabowski, John Wiley and Sons, 2004, Chapters 1-5.

Under normal conditions, all tissues and organs are nourished by an adequate and constant flow of blood through blood vessels to provide the necessary nutrients, transport oxygen and carbon dioxide, remove waste products, and defend against disease. In the normal non-disease state, the flow of blood is regulated by the muscle tension in the walls of the small vessels. This is controlled by the sympathetic division of the autonomic nervous system, i.e., the sympathetic chain or the SNS. The sympathetic chain has millions or billions of nerves in several divisions, each division doing different things. The divisions of the sympathetic nerves serve different end organs. In most organs not all of the small blood vessels are open at the same time. One part of the control by the sympathetic chain is to open and close the various small vessels so that no part of the organ is without adequate blood flow, even though most of the time most of the vessels are essentially closed. When muscles are at rest, not being commanded to contract, a small amount of muscle tension is maintained, by the sympathetic chain, which fires a few nerves at random all the time, so that the muscle does not go flaccid. All muscles, both voluntary and involuntary have a certain "tonus" or "tonicity" which is the state of normal tension when the muscle is at rest. It is believed that this serves the body by keeping the muscles ready to function in response to a stimulus.

The SNS coordinates cardiovascular, respiratory, digestive, excretory, and reproductive tissue and organ functions, and controls the blood flow to all by control of the wall muscles of the small blood vessels throughout the body. The SNS is often called the "flight or fight" system because it stimulates tissue metabolism, increases alertness, and generally prepares the body to deal with emergencies. Signals from the SNS affect the tonicity of the muscles in the systems. If the SNS is constantly sending excessive rather than normal levels of signals to the blood vessel wall muscles of an organ, the organ may be adversely affected by being chronically denied adequate blood necessary to function normally. Thus organ failure may occur not because of anything other than the sympathetic chain fires too often and the small blood vessels constrict preventing adequate blood flow to the organ, even while the blood pressure is normal. The inability of a muscle to reach the normal resting state is referred to by the inventor as hypertonus or hypertonicity. Hypertonus is defined as the condition where tissues or muscles cannot relax to normal when they are not being commanded to perform a function and should be at rest. This state of hypertonus or increase in resting tone can be any amount of increased tone from very little, to severe unrelenting spasm, or any level in-between. The state of unremitting hypertonicity of the small blood vessel walls prevents adequate blood flow to the organ, the consequences of which are discussed hereinafter.

Part of the inventor's discovery is that in a human subject exhibiting the signs and/or symptoms associated with reduced blood flow to an organ or tissue, the sign or symptom can be eliminated by administering an anti-herpetic compound, such as Formulas (I) or (II), to the subject for a period of time sufficient to increase the blood flow to the tissue or organ. This discovery was unusual in that there is presently no understood explanation as to why the administration of an anti-herpetic compound should cause improved blood flow to a subject's organ or tissue. While not wanting to be bound by a particular mechanistic theory, the inventor believes that he has developed a viable explanation of his discovery (introduced hereinbefore) and that the explanation leads to an invention that will be defined in its several aspects hereinafter. It is thought that constant over-contraction of the muscle tissues ("hypertonicity") of the arteriolar small blood vessels can be caused by herpetic activity in the sympathetic chain which causes the nerves controlling the arteriolar muscle tone to fire excessively and continuously. This constant over-contraction of the small vessel walls over time will result in the restriction of the flow of blood to the tissue or organ causing it to fail to perform its normal functions in the body. This restriction in blood flow due to hypertonicity can even damage or destroy the organ.

A subject having a disease correlated with hypertonicity generally will exhibit signs and/or symptoms associated with the disease. A sign is generally any abnormality indicative of a disease that is discoverable on examination of a subject; it is an objective indication of the disease. A symptom, on the other hand, is any departure from a subject's normal perception or sensation, but which may not be discoverable simply by examination of the patient. The major categories of signs or symptoms exhibited by a subject with a disease associated with abnormally high resting muscle tone (i.e., hypertonicity) may include tissue or organ inflammation, swelling, loss of function, scarring, destruction, and pain.

The blood vessel wall hypertonicity may be induced by the SNS constantly sending neuronal signals to the muscle tissues of the arteriolar blood vessels, thus heightening the normal tonus. It is generally accepted that the SNS is the preferred place in the human body that a herpes virus, e.g., HSV-II, survives for long periods of time. It is also generally accepted that once in the SNS, a herpes virus is never quiescent; it is always reproducing and releasing virus, even if no surface viral vesicles are present. The inventor reasoned that the presence of the virus activity in the nerve cells sufficiently affects the SNS at various segments to modify the signals sent to the target tissue. Excessive signals from the SNS keep the blood vessel wall muscles in a condition of hypertonicity. Thus, the hypertonicity of the muscle tissue is induced by constant herpetic irritation of the SNS, causing the SNS nerves to fire much more than they normally would. The constant irritation of the SNS is thought to be effected by (1) direct irritation of the cells by the virus or (2) the attack by the subject's immune system on the cells of the sympathetic chain in which the virus reproduces, or (3) both of (1) and (2). The ensuing constant hypertonicity of the muscle of the arteriolar vessels adversely affects the performance of the vessels and significantly reduces the blood flow to an affected tissue or organ, which can result in, amongst other things, inflammation, swelling, scarring, destruction, and/or pain in the tissue or organ affected by the reduced blood flow. Where the virus inappropriately tries to create vesicles or just release viral particles on other tissues that are similar to genital tissues, such as joint tissues, the virus releases "foreign viral proteins" on these tissues and the body responds by the immune system attacking the viral proteins. Because of an adjuvant effect, the immune system also attacks normal body tissues in the joints near or adjacent to where the viral particles are released. This attack by the immune system has been accepted in the past as the mechanism which causes all of the damage of autoimmune diseases and these other diseases that often, but not always present with autoimmune diseases.

The ongoing, SNS-induced hypertonus in the arteriolar blood vessels feeding tissues or organs of the human body is an explanation for a host of disease states presently having no prior explanation of their origins. It can thus be seen that certain disease states can be defined as diseases originating from the abnormal functioning of the sympathetic chain, i.e. over-active sympathetic chain syndrome ("OASCS") or under active sympathetic chain syndrome ("UASCS"). The diseases can be described as a condition in which the sympathetic chain is overactive and is sending out many more impulses than is normal or is under active and is sending out fewer impulses than is normal. This occurs both when the sympathetic chain is not receiving input and when it is receiving input from its environment. The sympathetic chain has nerves that carry messages into the chain, and in the case of sympathetically-mediated pain, the nerves of the chain forward the pain messages on to the brain. The sympathetic chain controls many body functions that are mostly automatic, i.e., autonomic functions of the body. As mentioned above, these functions include the resting tone of the body tissues, or tonus. This inventor has discovered a condition of the sympathetic chain (OASCS), which will not allow tissue such as muscles to relax to their normal resting state (they do not reach tonus), and a method of treating the condition. The inventor's discovery and further observations lead to an explanation of the origins of a large number of diseases of unknown cause, which often, but not always, present with autoimmune diseases. Treatment, processes, and systems in accordance with this invention appear more effective than other known treatment attempts and not only stops progression in certain diseases, but also returns tissue or organ function to normal where such function has been significantly reduced or lost. The tissues or organs affected maybe those of the eye, salivary glands, nose, heart, lungs, liver, gallbladder, stomach, pancreas, spleen, kidney, bladder, uterus, external genitals, and large and small intestines. No prior approved treatment ever recovered lost organ function, and the current state of medical knowledge is that organ function lost to this group of diseases, can never be recovered.

Thus, part of the invention is a new treatment for a large group of previously untreatable diseases, including all autoimmune diseases and other diseases which often present with autoimmune diseases, but not always. The cause of autoimmune disease and these associated diseases is unknown according to the current medical literature. As discussed above, the methods and systems of this invention are based upon a different theory of the cause and mechanisms of these diseases than current medicine proposes. The theory is that both autoimmune diseases and these other diseases are all caused by one or more herpes virus modifying the activity of the SNS, with HSV-II (genital herpes) being one of the worst offenders. As discussed before, it is accepted fact that the herpes virus, especially HSV-II, lives preferentially in the nerve cells of the sympathetic chain. It is also accepted fact that many viruses which often are inactive or dormant often for years after an initial infection. However, HSV-II continues to be active, reproducing and releasing virus at a low level, even when there are no obvious signs of virus activity, including herpetic vesicles on the surface of the body of the infected person. This is demonstrated by the fact that many people contract HSV-II even though the person of origin has no vesicles. It is estimated that up to 70% of new HSV-II infections occur while there are no surface vesicles.

Of all the viruses that have widespread distributions in the human population, the herpes viruses display the most aggressive long term continued residency in humans. The herpes family includes Varicella-Zoster (chicken pox-shingles), HSV-I, HSV-II, cytomegalovirus, Epstein-Barr virus and several others that infect humans. When the immune system fails or is suppressed a new presentation of the herpetic vesicle phase commonly results. This is not true for measles, and numerous other common viral illnesses. Herpes displays a preference for and an ability to survive in nervous tissue for long periods. Many of the signs or symptoms of the diseases treated in accordance with this invention are explained by limited focal irritation of the SNS. Herpes viruses display the ability to erupt focally in zoster (shingles) and HSV-I and HSV-II. Most children are infected within 5 years of birth and suffer a short episode of varicella (chicken pox). The immune system then suppresses the infection, which then becomes latent only to re-express itself after the age of 50 as shingles, a usually very localized presentation involving only one, two or three nerves. This expression almost inevitably occurs in immunosuppressed patients, such as AIDS (Acquired Immune Deficiency Syndrome) or transplant patients. HSV-II is thought to infect between 25% and 33% of all people in the U.S., according to the CDC. The expression of the most dramatic viral shedding stage of the virus is generally held in check by the immune system, but it represents in immunosuppressed patients, as the viral shedding vesicle eruptions. The detection of the presence or absence or a herpes virus is determined by employing methods known in the art, such as those described in 16207, which is incorporated herein by reference. See pages 20-22 of that document. Other examples include "HSV-2 Rapid Test Kit" (biokit USA); "HerpeSelect®" (Focus Diagnostics, Inc.), "ToRCH" (Trinity Biotech, Plc.), and various HSV studies performed by the University of Washington Virology Research Clinic.

This leads to one aspect of the invention, namely a method treating or preventing a disease in a human subject, where the disease originates from an abnormal functioning of the SNS, which method comprises administering on a daily basis to the subject a therapeutically effective amount of an anti-herpetic compound, e.g., a 2-amino purine derivative such as a compound represented by Formulas (I) or (II), for a period of time sufficient to alleviate signs or symptoms of the subject associated with the disease. Because the available data correlates the presence of a herpes virus in the subject with the abnormal function of the SNS, the herpes virus is implicated as a causative factor. The therapeutically effective amount of the compound is equivalent in activity to at least about 150 mg famciclovir per kg body weight of the subject per day. It will be recognized by one of skill in the art that famciclovir is a pro-drug for penciclovir, the entity that has activity in the human body. See for example the 2006 edition of the Physician's Desk Reference (PDR) at page 2207. The very high dose treatment is thought to suppress the viral activity in the body. This stops both the production of viral proteins, which is thought to be one cause of the immune system attack on tissues, and allows the sympathetic chain to return to normal function, or firing rates which stops all of the diseases caused by the abnormal functioning of sympathetic chain activity. This in turn results in an improvement in the signs or symptoms of the subject being treated, for example the reduction of pain or inflammation.

Representative 2-amino purine derivatives are approved only for use to treat and suppress herpetic vesicles. For famciclovir, the FDA-approved dose may be up to 1500 mg per day for a few days for certain conditions (see the PDR, page 2210). This would amount to about 15 mg/kg per day for a 100 kg person. It is normally given when the tingling occurs which precedes the vesicle formation. This invention is to use doses of a compound of Formulas (I) or (II), or pharmaceutically acceptable salt thereof, that are equivalent to more than 10 times or higher than the recommended dose for the suppression of vesicles. The drug is taken at regular intervals throughout the day, at least once, but generally about 3 to 10 times a day to maintain an appropriate, therapeutically effective activity level in the blood stream, not just when "tingles" present. Doses every 6 hours has been found to be useful, e.g., doses equivalent to 3750 mg of famciclovir per dose, 4 times a day. This is equivalent to 15,000 mg per day or higher of famciclovir for a 100 kg subject. These equivalently higher doses of famciclovir are required because these drugs are extremely insoluble in cell membranes, thus very high doses must be ingested for a small but adequate amount to get inside the cells of the sympathetic chain to suppress or significantly reduce activity of virus reproduction, compared to the amount approved by the FDA that is adequate to suppress most herpetic vesicles on the surface.

The possibility of administering standard doses of anti-herpetic drugs to treat autoimmune disease was suggested because a few people taking 2-amino purine derivatives for suppression of vesicles, reported that they had some slight relief of autoimmune symptoms. Several investigators attempted to determine if a 2-amino purine would help with autoimmune symptoms. They all reported no benefit in double blind trials, and some reported increased symptoms.

The manufacturers of commercially available anti-herpetic drugs all stated that doses higher than those approved for vesicle suppression were dangerous to the kidney, and might cause kidney shutdown. See, for example the 2006 PDR at page 2209 under "Precautions." This inventor reviewed the data upon which the dose limitation was based and concluded that the data did not support the alleged danger. He then started trying higher and higher doses, and discovered that it was true that doses between 2× and 8× did increase the symptoms the patient was suffering particularly pain, and GI symptoms. He developed a way to deal with these problems, and patented in '114 his discoveries with these doses.

While the treatment of autoimmune disease using high levels of the anti-herpetic drugs taught in patent '114 provided noticeable improvements in a patient, signs or symptoms lingered even with ongoing treatment. Knowing the warning of the anti-herpetic drug labels that were on the market against using higher doses, increasing the dose even further was definitely contraindicated. However, the inventor was confronted with a problem of a subject presenting with extremely painful migraine type headache, which was diagnosed to be aseptic (not bacterial) meningio-encephalitis. In spite of the general knowledge of the state of the art warning that using higher doses could be dangerous to the kidneys, the inventor administered much higher doses of, e.g., famciclovir to the subject and found that not only were the signs or symptoms of the encephalitis alleviated, but also the other signs or symptoms of other diseases that often present with autoimmune disease were reduced to near zero. The higher doses were much more effective at suppressing the signs or symptoms of autoimmune disease than the doses in '114, and resulting much lower side effects particularly the increased pain and other distressing symptoms such as sudden bowel emptying with each dose which often occurred at the doses in patent '114. The inventor also discovered that by using the much higher doses of famciclovir than previously taught in '114, the need to titrate a subject to tolerance of the drug could be avoided, that is the higher doses were effective at ameliorating the signs or symptoms of the disease without the accompanying pain of starting at a low dose and increasing it to a therapeutically effective level, as experienced with the doses of '114. While not wishing to be bound by a particular theory, it is thought that by regularly administering the higher levels the drug, a subject avoids a fluctuating blood level that can add to the irritation of already irritated nerves by major influxes of drug at a high level after having been at a lower level in the subject. The compounds of Formulas (I) or (II) appear to provide further benefit for treating these conditions.

This treatment is useful, not only in stopping the progression of the diseases, but in returning more of organ function previously lost. Text books claim that organ function lost to these diseases can never be recovered, but this treatment has succeeded in recovering nearly all lost organ function. One of the diseases for which a large return of function appears achievable is progressive loss of renal function by unknown cause, but suspected to be autoimmune disease related. A clinical laboratory measure of kidney function is creatinine clearance. Creatinine is the metabolic product formed from creatine when food is converted to energy. Creatinine is produced at a steady state and is affected very little by diet or normal physical activities. When a subject's kidneys are damaged and/or cannot function normally, the amount of creatinine excreted in the subject's urine decreases while its level in the blood increases. Thus, the blood level of creatinine indicates how well the kidneys are working A higher than normal blood level of creatinine usually means the kidneys are not functioning properly. A creatinine clearance test is a calculation of the renal filtration rate, and is performed both on a blood sample taken from the subject's vein and on a sample of urine collected over 24 hours. Normal creatinine clearance (CrCl) indicates normal renal function; reduced CrCl indicates reduced renal function. For example, a blood creatinine level of 3 shows a definite malfunction of the kidneys. Treatment with very high doses of famciclovir returned the kidney function in one patient from a creatinine clearance level that was ~29 mL/min, near to requiring dialysis (20 mL/min of creatinine clearance), to near normal (more than 140 mL/min). The doses of '114 only returned the renal function to ~89 mL/min, in this same patient. While text books claim that it is impossible to recover any significant amount of renal function lost to these diseases, this new treatment suggests otherwise. These diseases are one of the more common causes of renal failure resulting in dialysis or premature death often in people about age 40, sometimes less. The reason the current thinking appears to be wrong is because the kidneys and other organs do not stop functioning normally because of autoimmune attack upon the cells, as currently believed. The organs stop functioning because the sympathetic chain causes over or under firing levels from these nerves, which are irritated by the herpes virus. This increased SNS firing causes hypertonus of the arterioles, and prevents normal blood flow to the kidneys, and thus creatinine clearance is reduced, but can be restored when blood flow is restored by controlling the herpetic activity in the sympathetic nerves, by the treatments of this application. And, it is this alteration in firing, i.e., abnormal functioning of the SNS, particularly the increase in firing that is the cause of most of the lost organ function, such as renal failure. This high level of restoration of previously lost renal function in the inventor's previous work is especially remarkable, considering that it was previously thought, that in autoimmune disease, many nephrons are irreversibly destroyed by inflammation from direct autoimmune attack on the kidneys. Therefore no restoration of the kidney function was thought to be possible. However, it has been demonstrated previously that with high enough amounts of famciclovir, the inflammation subsides and kidney function improves to previously unseen levels. Presumably, this very significant improvement of kidney function is due to the previous lack of flow of blood to the kidneys due to hypertonus of the arteriole vessels feeding them. As a result of reduced blood flow, some of the glomeruli may be inflamed to the point of limited functionality or no functionality at all, but are then able to resume more normal functioning when blood flow increases and their inflammation subsides. The progression of organ damage can be slowed, the inflammation stopped, and damaged and not destroyed tissue can repair itself with return of function that was previously lost. As the measured kidney function improves a parallel process occurs in other affected tissues or organs, with a diminution of the visible inflammation, swelling, pain, grinding and clicks in the afflicted articular joints. Renal function tests that evaluate the severity of reduced kidney function can be found in The Merck Manual, $17^{th}$ Edition, at pp. 1809-1810.

The treatments of this invention using a compound of Formulas (I) or (II), or pharmaceutically acceptable salt thereof, are useful to suppress the viral activity in the cells of the sympathetic chain, and the firing levels of the sympathetic nerves return to normal. As discussed hereinbefore, the sympathetic chain controls, i.a., the flow of blood to the organs, by control of the muscles of the small blood vessels in the organs. The OASCS can restrict the blood flow to an organ so severely than it cannot function, and eventually result in organ death. The model for this is Raynaud's disease of the hands and feet. The cause of Raynaud's is unknown and there is no effective treatment, according to the medical literature. See The Merck Manual, $17^{th}$ Edition, page 1790. As an anti-herpetic drug, a compound of Formulas (I) or (II), or pharmaceutically acceptable salt thereof, when administered appropriately, can successfully return the blood flow to normal in a subject having HSV-II and Raynaud's disease, and can return renal function to normal.

The treatment of this invention may be useful for treatment of conditions that are minor or major. For example if the muscles that refuse to relax normally are in the back or leg, the result can be a "charley horse" or an annoying spasm on the peripheral muscles. This might be annoying, but not very dangerous. However, if the area is the sphincter of the outlet to bile duct, billiary inflammation progressing to infection and death can occur. If the area affected is the sphincter to the outlet to the urinary bladder, the condition might have been previously ascribed to Benign Prostatic Hypertrophy (BPH): the outlet refuses to release and the bladder will not empty properly, with the symptoms of hesitancy, small stream, incomplete emptying, and bladder dilatation. The usual treatment for BPH is the removal of some of the prostate tissue, which is believed in current medical thinking to be preventing the sphincter from relaxing normally. However, it should be noted that this procedure often and usually does remove some of the bladder sphincter muscle, weakening it. That is one way to relax a muscle in hypertonus, but an extreme technique. By employing a treatment of this invention with an appropriate dose of an anti-herpetic compound of Formulas (I) or (II), or pharmaceutically acceptable salt thereof, all of the symptoms of BPH may be suppressed. This treatment suppresses the OASCS of the nerves controlling the tonus of the bladder sphincter and normal function returns without cutting the muscle to weaken it.

The diseases that are included within the OASCS and UASCS can be organized into seven categories based upon similarity of the conditions caused. All are caused by sympathetic chain over activity except for #7, which is caused by under activity of the sympathetic chain:

1. those involving the pain system of the sympathetic chain;
2. those involving ongoing or chronic hypertonicity of the muscles;
3. those involving sudden muscle spasm-causing hypertonicity;
4. those involving a combination chronic and sudden hypertonicity;
5. those leading to sleep disturbance or restless leg syndrome;
6. those leading to severe fatigue; and
7. those involving the loss of sympathetic nerve function, with loss of control of some autonomic muscles, or loss of sensation, or both.

The following discussion addresses the categories and includes diseases presently identified. Other diseases not specifically mentioned here may be recognized by one of ordinary skill.

1. Diseases Relating to the Pain System of the Sympathetic Chain

One of the divisions of the sympathetic chain is an extensive group of nerves which report pain to the brain, the afferent nerves. The overactive sympathetic chain syndrome (OASCS) can involve the afferent pain system of the sympathetic chain, resulting in chronic pain from mild to severe, and hypersensitivity to even light touch which can cause severe pain. Examples include most severe chronic pain syndromes and trigger point syndromes such as fibromyalgia, and severe irritable bowel syndrome, many cases of back pain of unknown origin (e.g., sciatica), dyspareunia, and migraine headaches. Tinnitus is another condition in this category. There are many more diseases and pain conditions that are caused by OASCS of the pain nerves of the sympathetic nerve chain, these are just a few examples. The knowledge of even the existence of these disorders is so poor among physicians that often the patients are labeled as malingerers, or wanting pain killers to get high, or having some psychiatric problems. This treatment effectively suppresses as much as 95% of the pain, previously not treatable even with high doses of morphine or similar substances. It is possible that Howard Hughes suffered from this condition, which could explain why he spent his last decade lying in bed with no clothes on, and self medicating with morphine. It is believed that his intent was merely to suppress severe pain from the OASCS of the pain nerves. Pain clinics are filled with people seeking relief from these conditions. This treatment may offer significant relief.

2. Diseases Relating to Chronic Hypertonicity of the Muscles

The sympathetic chain controls the blood flow to all of the tissues and organs of the body by controlling the muscle tension in the muscle walls of the blood vessels which supply the tissues and organs. When the sympathetic chain nerves that control the blood flow fire excessively, the small blood vessels can never relax normally in the affected regions of the body. Essentially what this inventor is proposing is that conditions analogous to Raynaud's phenomenon occur not just in the hands and feet, but in various internal organs. Just as this treatment may totally suppress the cold and pain of hands and feet in Raynaud's, it increases blood flow to various organs, including the kidneys. Just as the hands and feet return to normal color and warmth with the blood flow returned, the kidneys again function when normal blood flow is restored to them. This inventor proposed that Raynaud's and much of the organ function lost of "autoimmune diseases" is actually caused constant excessive muscle tension (hypertonus), that prevents adequate blood flow to the organ for it to maintain function. If the hypertonus is severe enough the organ may lose all function and "die". As discussed herein, the inventor believes that the excessive firing is caused by the herpetic viruses particularly HSV-II, which lives preferentially in the sympathetic chain nerves, and is always active proven by the production of infectious viruses, even when vesicle are not present. Similar to shingles, one nerve may be highly afflicted causing hypertonus, and the next functioning relatively normally. This selection by nerve(s) is how the hypertonus can be so selective as to afflict only one or two organs. A patient may experience a condition of mild to severe chronic failure of muscles to relax to normal resting tonus when they are not activated by action commands. The treatment of this invention suppresses OASCS and allows muscles in hypertonus to return to near normal resting tone or tonus. An example is hypertonus of the muscle walls small blood vessels is Raynaud's disease which prevents adequate blood flow to the tissues of the hands and feet. This condition causes severe pain, cold, dark red or blue hands and/or feet, which can progress to tissue death and loss of chunks of the fingers, hands, toes and/or feet. This limitation of blood flow appears to be the cause of many different diseases resulting from organ dysfunction and eventual failure to sustain life. Chronic renal failure with or without autoimmune disease is a good example. Another example is the chronic spasm of a coronary artery (Prinzmetal's angina), which may require a stent to keep a segment of a blood vessel wall open where hypertonus occurs. This is a condition often seen in patients having balloon dilation of their coronary arteries. Another example is scoliosis. This is where chronic unrelenting spasm in the paraspineous muscles in children cause the forming bones to be distorted by the unremitting spasm into an S curve. One part of the curve is the area of spasm. The bend of the S in the spine is compensation so that the victim holds their head upright, rather than being bent to the side, without a compensating curve. Severe kyphosis (deformity of the spine characterized by extensive flexion, such as a 'hump back') in adults is caused by severe chronic spasm of the entire thoracic spine muscles which bends the back in a forward curve causing the neck to protrude forward of normal, and the same for the abdominal region. Another condition that can be treated in accordance with this invention is Dupuytren's contracture in which the tendons and muscles of the middle and third fingers cannot relax and thus are forced into a permanently "clawed" position. Additional conditions include pulmonary hypertension and/or pulmonary fibrosis. Other diseases caused by OASCS will be apparent to one of skill in the art in light of the teachings of this application. All of these are examples of muscles that can not relax to normal resting state, and the diseases or conditions that are caused by this inability to relax the muscles.

3. Diseases Relating to Sudden Muscle Spasm Syndrome ("SMSS") Hypertonicity.

The SMSS hypertonicity is part of the OASCS and can lead to spasm of any of the muscles of the body. The muscles suddenly go from relatively normal resting tone to high spasm in an instant, often causing severe pain, and if it is in a critical area it might cause serious secondary effects. The SMSS results in a subject experiencing sudden spasm of any of the muscles of the body. Often this spasm will relent after a few (10) minutes, but sometimes it continues for many minutes (120 or more) before it will suddenly relax to normal. The difference between OASCS caused hypertonus and SMSS, is that SMSS causes the muscles to suddenly go from relatively normal resting tone to high spasm in an instant, often causing severe pain. If the spasm is in a critical area it might cause serious secondary effects such as coronary artery contraction. Sudden coronary artery spasm, which often causes heart damage and death, is one of the most common mechanisms of death in the US. This is one of the causes of what is called a "heart attack." Some other examples are torta collis, (where the muscles of the neck suddenly spasm twisting the head to one side, and often will not relent for many minutes to hours), nutcracker esophagus syndrome (where the muscles of the esophagus will suddenly spasm down on the food, and cause extreme pain, usually reverting to normal within 30 minutes), much back pain is caused by SMSS. Another example is sudden emptying of the bladder or bowels without much control.

4. Chronic and Sudden Onset Hypertonicity

In some cases, conditions are not easily categorized into either category 2 or 3 show some ongoing or chronic hypertonicity but also some spasm. An example of this would certain gastro-intestinal dysfunction and inappropriate bladder activity, such as sudden emptying of the bowels or bladder. The symptoms in the bladder are often blamed on the increased size of the prostate, often called benign prostatic hypertrophy or BPH, which is discussed hereinbefore.

5. Sleep Disturbance and Restless Leg Syndrome

Severe sleep disturbance can be caused by inability to relax the axial muscles due to hypertonus. This problem is not appreciated by those without hypertonus of the muscles, but it is necessary for the somatic muscles to relax to a predetermined level, before sleep will commence. Hypertonus can prevent that relaxation and prevent sleep. Both sleep disturbance and restless leg syndrome may be caused by diseases of the SNS, as discussed above, and can be suppressed by the treatments of this invention.

6. Severe Fatigue

Severe fatigue often cannot be relieved by any current treatment. This is probably a function of OASCS and hypertonus caused by a herpetic infection of the SNS leading to limited blood flow. Being in a constant state of hypertonicity prevents relaxation and rest or sleep, which in turn leads to constant fatigue.

7. Loss of Sympathetic Nerve Function

The loss of sympathetic nerve functions, can occur with a loss of control of some function of some autonomic muscles, or loss of sensation or both. This is not as common as 1 through 6, above. And, the effects are usually not as severe. One example is the loss of control of the soft palate, either partial or complete which can cause severe snoring, and is part of the sleep apnea syndrome, and also can cause a snorting sound when talking or laughing, or can cause food to get caught under the soft palate. Another condition is cranial nerve palsies as discussed in the Sixteenth Edition of the Merck Manual at page 2395. Another is acholasia of the esophagus, where the esophagus just does not contract normally, but does not spasm as in nutcracker esophagus, but is essentially flaccid and inactive in the lower half which is controlled by the sympathetic chain. This new treatment may effectively suppress progression of all of these conditions.

The inventor has discovered as part of his invention that administration of an anti-herpetic compound of Formulas (I) or (II), or pharmaceutically acceptable salt thereof, must continue at the desired level even after the signs or symptoms of OASCS have been initially relieved, i.e., if the next dose of this treatment is delayed for more than 6 to 12 hours, the signs or symptoms of the disease conditions may return, which will remind the patient when it is time to take the next dose.

The inventor's discovery and observations leads to another aspect of this invention, which is a method for preventing or treating a disease of a tissue or organ originating from an abnormal functioning of a subject's SNS, such as decreased blood flow through blood vessels to a tissue or organ. The method comprises (a) administering an anti-herpetic compound, e.g., Formulas (I) or (II), or pharmaceutically acceptable salt thereof, to a human subject having an herpes virus infection, such as HSV-II, for a period of time sufficient to increase the blood flow to the tissue or organ affected and (b) maintaining the administration of the compound to the subject beyond the period of time so that the subject's SNS is normalized, i.e., to achieve a normal tonus of the blood vessels feeding the affected tissue.

Once the intracellular activity of the virus is inhibited by the adequate concentration of an active compound such as penciclovir, the irritation of the sympathetic neurons is decreased, and the abnormally increased firing of the sympathetic neurons is diminished. When the sympathetic pain neurons and tonus neurons decrease firing, the pain and the abnormal hypertonus of muscles diminish or disappear. When the smooth muscles relax to normal tonus, the entire group of signs or symptoms caused by their abnormal contraction abates. As a secondary effect, the symptoms caused by diminished blood flow also abate. The pain caused by abnormal firing of the sympathetic neurons, as well as pain caused by tissue hypoxia, also disappears.

It will be appreciated that this invention has two aspects: treatment and prevention. The treatment aspect is directed at conditions that have progressed significantly and organ or tissue functionality has been reduced, with the subject exhibiting advanced signs or symptoms of the condition. The prevention aspect is directed at conditions that have not progressed significantly and organ and tissue function may be slightly reduced, but the subject's signs or symptoms are not as pronounced. Thus, the preventative aspect could be described as a method for preventing the advance of a disease associated with reduced blood to an organ or tissue, which method comprises (a) examining a human subject for a sign or symptom of the disease, (b) determining if the patient is infected with a herpes virus, and (c) if the subject hosts such a virus and exhibits such a sign or symptom, administering a compound of Formulas (I) or (II), or pharmaceutically acceptable salt thereof, to the subject for a period of time sufficient to prevent the advance of the disease.

Whether the method is to treat or prevent the disease, a compound is administered for a time and at a level that results in amelioration of the signs or symptoms of the disease and allows the subject to function at a normal level. The levels and amount of time that will be needed to achieve results may vary from person to person and can be determined by a physician versed in the arts of administering drugs and evaluating patients. Reduction in signs or symptoms may be seen within one day in some cases but generally a compound will have to be administered for at least a week or more to see positive results. Because the herpetic infection stays dormant in the SNS, the administration will be ongoing at a level that is shown to be effective for a particular individual in most cases for the remainder of a subject's life. The method is useful for both male and female subjects. At very high does, the male sex drive may be significantly reduced because of the effect of the compound on the male testes. Females should not see such problems.

With regard to approved use of antiviral drugs today, the prevailing opinion in the field is that anti-herpes drugs are dangerous for patients with impaired kidney function. The drug makers (Novartis for FAMVIR® and GlaxoSmithKline for ZOVIRAX® and VALTREX®) teach reducing the amount of the drug in proportion to kidney function as measured by creatinine clearance. For example, a person with clearance that is 50% of normal should get 50% of the Famvir® dose for a genital herpes outbreak. If the clearance is at 25% of normal, the patient gets a 25% dose of Famvir®. For Zovirax®, the manufacturer recommends taking the same dose, but at longer intervals. A person with 50% kidney function would take the drug every 8 hours instead of every 4 hours. For Valtrex®, both the reduction in dose and lengthening the time interval are recommended.

The amount of a compound of Formulas (I) or (II), or pharmaceutically acceptable salt thereof, administered to a subject in need thereof in accordance with this invention will be at a level sustained throughout the day to see the desired results. Depending on the individual, the compound is administered in a manner that maintains an effective level throughout the day, generally from 3 to 10 times a day to give the total amount needed for the subject being treated and to maintain the compound at a high enough level through the day. Three to six times a day is useful, with four equal doses every six hours being particularly useful. The doses are higher than those doses of known compounds generally used for the treatment of herpes viruses such as HSV-II as taught for other compounds in International Publication WO 2006/127217 A2. The compounds are administered at a rate that is equivalent to at least 150, and preferably 300-400 mg/kg famciclovir per day means taking the drug every six hours, i.e., four times in a 24-hour period, so that the total amount taken in the 24-hour period would be equivalent in activity to 150-400 mg famciclovir per kg of body weight.

If high doses of anti-herpes drugs are administered before the damage and scarring of tissue or organ takes place, particularly the blood vessels supplying these organs, the function of the organs can be returned to near normal when the spasms and hypertonus are relieved.

The compounds of Formulas (I) or (II) have an increased likelihood of reaching the cytoplasm of neurons where the virus is acting. The concentration of the anti-herpetic drugs outside the nerve cells needs to be high in order to achieve significant concentrations inside these cells. To be effective, the drug must penetrate the cells where the viral replication takes place and tie-up the viral thymidine kinase, which is the target for the anti-herpes drugs. Famciclovir is found to be particularly effective, but other compounds set forth hereinafter will also work, depending on the patient and progression of the condition. The drugs will be administered at a level that is equivalent in its effect to 150-400 mg famciclovir per kg of the subject's body mass per day, generally divided into 4 doses.

It is known from International Publication WO2006/127217 A2 that compounds of Formula (II) are highly water soluble and notably more stable to aqueous hydrolysis, particularly between pH 6-10, compared to valacyclovir. While pharmacokinetic studies of compounds of Formula (II) have not yet been published, and accepting that a complex interplay of physiological functions affects the bioavailability of any drug, it is yet conceivable to those skilled in the art that the enhanced solubility and stability characteristics mentioned above may result in better absorption of such compounds into the plasma, with a longer residence time, resulting in a higher oral bioavailability of the active parent drug acyclovir, compared to valacyclovir (55±9%) and famciclovir (77±8%). If true, then it is possible that lower than expected doses of compounds of Formulas (I) or (II) would be needed to achieve doses equivalent to the 150 mg/kg/day famciclovir comparator.

Preventing herpes viral shedding, prodrome, and vesicle outbreaks.

The inventor in this application is aware of the prior art teaching of U.S. Pat. No. 5,559,114 ("'114") and International Application No. PCT/US95/16207 ("16207") that describe the treatment of certain autoimmune diseases using higher than FDA-approved amounts of certain 2-amino purine derivatives. According to the teachings of the '114 patent and the 16207 application, one compound useful was acyclovir (or its precursor valacyclovir) at a level of 20 to 50 g per day for a 100 kg subject (or 5-10 g of valacyclovir). Another compound was famciclovir (the precursor of penciclovir) at about 4-10 g per day for a 100 kg subject (up to 12 g/kg/day). In following the treatment regime so taught for a subject having HSV-II infection and with the drug used to suppress autoimmune disease signs or symptoms, the inventor of the present invention observed that although the signs or symptoms of the subject's autoimmune disease improved, the subject continued to experience discomfort even if the high dose regimen of famciclovir described in the '114 patent was followed for a number of years. In addition, the subject continued to have prodrome episodes, vesicle outbreaks, and viral shedding. The prodrome is the sensation of tingling, pain or both in an area where the herpetic vesicles will appear within 24 to 48 hours. This is a very reliable signal that vesicles will appear on schedule. Vesicles are blisters or ulcers that appear on the skin or various mucous membranes as a result of the virus's replication process destroying cells that it has invaded. Viral shedding means that the virus is active on the skin, even though there is no prodrome or vesicle formation, and can be transmitted to another subject through skin contact, kissing, sexual intercourse, or oral sex.

The inventor has noticed an additional benefit to this treatment. It is well known and accepted that at least one herpes virus (HSV-II) produces infectious virus constantly even when vesicles are not present on the skin. Currently it is accepted by the medical profession that at least 70% of new infections of HSV-II in persons not previously infected occurred when the infected partner did not have vesicles, and had not recently had vesicles. This phenomenon of releasing virus without vesicles is referred to as "viral shedding", which is shorthand for viral shedding without vesicles.

Viral shedding has two consequences, infection in the host of nerves not previously infected, and transmission to a new previously uninfected person. The mechanism of production and release of virus is the same for both. This inventor has noticed that infection of new nerves in a person with infection of other nerves is frequently accompanied by sharp pain which is felt in the area innervated by the nerve which is newly infected. In persons not previously infected there is a similar sensation, as the initial infection is always felt as a sharp pain in a region, which often will form vesicles 24 hours later. However, in the person who was previously infected and has an ongoing immune response, the transmission of virus to a previously uninfected nerve will produce the sharp pain, but vesicles only form a small portion of the time, estimated to be less than 20% in patients with competent immune systems.

At doses of 300 mg/kg/day famciclovir all of these sensations are suppressed and no new vesicles form on the surface of the person with an ongoing infection of HSV-II. This inventor interprets this to mean that viral shedding has been reduced dramatically, at least 90%. It is probably that viral shedding has been stopped completely.

This has strong implications as it demonstrates a technique where persons infected with a herpetic virus, including HSV-II can suppress the virus shedding from them, and thus prevent spread further in their own bodies, and to uninfected partners. Prior to the inventor's discovery there was no technique which was good and effective at preventing the spread of this virus from infected, even without current or recent vesicles, to the uninfected. Probably the best technique was a condom, and of course many people refuse to consistently use a condom, even when there is risk of the spread of venereal diseases. It is accepted by the medical community that AIDS is spread by breaks in the skin. Herpetic vesicle lesions are one skin break portal through which AIDS is spread. Thus, suppressing the spread of herpetic viruses has benefits beyond stopping the spread of herpes and the diseases that it causes, which this inventor believes includes most if not all diseases previously referred to as "autoimmune diseases" and diseases of inappropriate under or over activity of the sympathetic chain caused by the herpetic virus living and reproducing in the cells of the sympathetic chain. Using this treatment to prevent the HSV-II infection of new patients will reduce the number of patients with that AIDS portal to entry in patients not previously infected with AIDS.

While vesicle formation and prodrome may be suppressed by administering a compound of Formulas (I) or (II), or pharmaceutically acceptable salt thereof, equivalent to famciclovir at 150 mg/kg/day, the amount of a compound of Formulas (I) or (II) may vary from individual to individual depending on a number of factors, such as age, sex, condition of the immune system, and others that a doctor may determine. Thus, the method and the product are useful in both male and female, young and old, and various ethnic groups. The inventor has observed total suppression of the vesicle formation with an ongoing dosage of 300 mg/kg/day famciclovir. Additionally, a dose level of a compound of Formulas (I) or (II) that suppresses totally all of the sensations of virus release and new nerve infection in a patient suffering with HSV-II infection would be equivalent. It is reasonable to conclude these treatments suppress vesicle formation, prodrome, and viral shedding without vesicles.

It has been previously noted that patients with autoimmune disease may occasionally feel better when they are prescribed anti-herpes drugs for cold sores or genital herpes. Following up on this observation, there have been attempts to treat autoimmune disease with traditional and higher than recommended doses of these drugs. For example, the '114 patent teaches taking up to 64 g acyclovir per day of or up to 12 g famciclovir per day. For "traditional" herpes outbreaks, the recommended maximum dose for famciclovir (FAMVIR®) is 2 g per day. For acyclovir (ZOVIRAX®) the recommended maximum dose is 4 g per day. No observations were made that the doses of '114 caused significant reduction in prodrome or in the outbreak of vesicle formation in a subject with herpes infection.

The '114 patent teaches that at a preferable dose between 40 and 50 g acyclovir per day controlled pain, muscle spasms, joint tenderness and the butterfly rash in a lupus patient. The '114 patent also teaches that the same effect can be obtained with 10-12 g famciclovir per day, because of greater solubility and bioavailability of this drug as compared to acyclovir. However, even at that level the subject still continued to experience prodrome and vesicle outbreak.

Another aspect of the present invention involves administering a compound of Formulas (I) or (II), or pharmaceutically acceptable salt thereof, at dosages that are the equivalent of famciclovir at doses of at least about 150 mg/kg/day (and up to about 400 mg/kg/day), preferably divided into four doses taken every six hours. At this level new vesicle formation is eliminated, as well as prodrome sensations. And, this also eliminates most, if not all viral shedding without vesicles being present. Taking the equivalent of 300-400 mg/kg famciclovir per day means taking the drug every six hours, i.e., four times in a 24-hour period, so that the total amount taken in the 24-hour period equals 300-400 mg/kg usually totally suppresses prodrome, new vesicle formation, ongoing chronic pain, as well as reducing viral shedding. The viral shedding is reduced to 10% or less of the level seen in the absence of treatment.

It takes extremely high doses of the anti-herpes drugs outside the nerve cells in order to achieve significant concentrations inside these cells. To be effective, the drug must penetrate the cells where the viral replication takes place and the viral thymidine kinase, which is the target for the anti-herpes drugs.

Treating Herpes Viruses.

Certain compounds of Formula (I), or pharmaceutically acceptable salt thereof, are novel compounds and thus are not only useful for diseases originating from an abnormal SNS or preventing prodrome or vesicle outbreak, but are useful for treating standard Herpes outbreaks. Lower levels of the compound may be used for treating Herpes Simplex virus in accordance with methods known in the art for products such as ZOVIRAX, FAMVIR, VALTREX, DENAVIR, and the like.

The method is particularly useful for treating a Herpes HSV1, HSV2, or HZV for a compound of Formula (I) when derived from Penciclovir. For a compound of Formula (I) derived from Ganciclovir, the compound is particularly useful for treating cytomegalovirus or herpes simplex keratitis.

The novel compounds that are useful in this aspect of the invention are those of Formula (I), or pharmaceutically acceptable salt thereof, wherein Formula (I) is

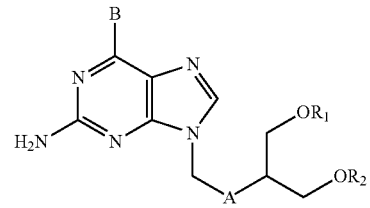

wherein A is $CH_2$ or O; B is H, Cl, alkoxy of 1-6 carbon atoms, phenoxy, phenylalkoxy where alkoxy is 1-6 carbon atoms, $NH_2$, OH or SH; $R_1$ is

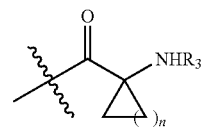

wherein n is 1-4 and $R_3$ is H or alkyl of 1-4 carbon atoms; and $R_2$ is independently H, $C(O)R_5$ where $R_5$ is alkyl of 1-5 carbon atoms, $C(O)CH(NH_2)R_4$ where $R_4$ is H or alkyl of 1-4 carbon atoms, proline, hydroxyproline, or

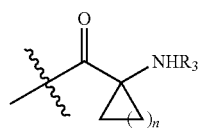

wherein n and $R_3$ are as defined.

The compounds are administered in a manner as discussed in U.S. Pat. No. 4,199,574 to Schaeffer, issued Apr. 22, 1980; U.S. Pat. No. 4,355,032 to Verheyden, et al. issued 19 Oct. 1982; U.S. Pat. No. 4,957,924 to Beauchamp, L. issued 18 Sep. 1990; U.S. Pat. No. 5,059,604 to Krenitsky et al., issued Oct. 22, 1991; U.S. Pat. No. 5,246,937 to Hamden et al., issued Sep. 21, 1993; U.S. Pat. No. 5,250,688 to Hamden et al., issued Oct. 5, 1993; and U.S. Pat. No. 5,075,445 to Jarvest et al., issued Dec. 24, 1991, each of which is incorporated by reference herein. Useful guidance may also be found in International Publication WO 2006/127217 A2, published Nov. 30, 2006, which is also incorporated by reference. The effective amount to administer will be less than that discussed previously herein, and may range from about 0.01 mg/kg body weight per day to about 100 mg/kg body weight per day.

Compounds Useful in the Invention

The anti-herpetic compounds that are useful for treating diseases in accordance with this invention are exemplified by those represented by Formulas (I) and (II) below.

Formula (I) is as follows. Some of the compounds of Formula (I) are believed to be novel.

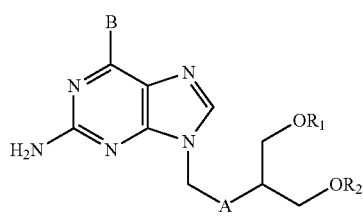

wherein A is $CH_2$ or O; B is H, Cl, alkoxy of 1-6 carbon atoms, phenoxy, phenylalkoxy where alkoxy is 1-6 carbon atoms, $NH_2$, OH or SH; at least one of $R_1$ and $R_2$ is independently $C(O)CH(NH_2)R_4$, proline, hydroxyproline, or

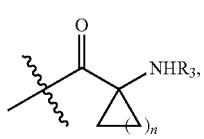

particularly the latter, wherein $R_4$ is H or alkyl of 1-4 carbon atoms, n is 1-4, particularly 1, and $R_3$ is H or alkyl of 1-4 carbon atoms, particularly H; and the other of $R_1$ or $R_2$ is independently H, $C(O)R_5$ where $R_5$ is alkyl of 1-5 carbon atoms, $C(O)CH(NH_2)R_4$, proline, hydroxyproline, or

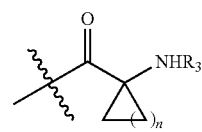

wherein n, $R_3$ and $R_4$ are as defined.
Formula (II) is as shown below.

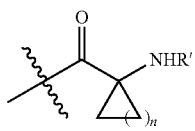

wherein A is OH and R is

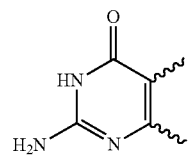

wherein n is 1-4, and R' is H or alkyl of 1-4 carbon atoms.

It should be noted that for Formulas (I) or (II) where A is designated as OH, an alternative representation of the purine ring would be as follows:

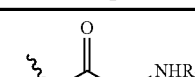

Representative examples of Formula (I) that find use in the invention of this application include those set forth in Tables 1-3. Representative examples of Formula (II) that find use in the invention of this application include those set forth in Table 4. Others will be apparent to one of ordinary skill upon applying the teachings and description relating to Formulas (I) or (II), above and below.

TABLE 1

| Mono-esters of Formula (I) | | | | | | | |
|---|---|---|---|---|---|---|---|
| A | B | $R_1$ | $R_2$ | n | $R_3$ | $R_4$ | $R_5$ |
| $CH_2$ | H | H | 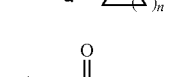 | 1 | H | — | — |
| $CH_2$ | Cl | H | 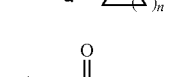 | 1 | H | — | — |

TABLE 1-continued

Mono-esters of Formula (I)

| A | B | R₁ | R₂ | n | R₃ | R₄ | R₅ |
|---|---|---|---|---|---|---|---|
| $CH_2$ | $NH_2$ | H | [C(O)-cyclopropyl(NHR₃)] | 1 | H | — | — |
| $CH_2$ | OH | H | [C(O)-cyclopropyl(NHR₃)] | 1 | H | — | — |
| $CH_2$ | OMe | H | [C(O)-cyclopropyl(NHR₃)] | 1 | H | — | — |
| $CH_2$ | OPh | H | [C(O)-cyclopropyl(NHR₃)] | 1 | H | — | — |
| $CH_2$ | OH | H | [C(O)-cyclopropyl(NHR₃)] | 1 | Me | — | — |
| $CH_2$ | OH | H | [C(O)-cyclopropyl(NHR₃)] | 1 | Et | — | — |
| $CH_2$ | OH | H | [C(O)-cyclopropyl(NHR₃)] | 1 | i-Pr | — | — |
| O | H | H | [C(O)-cyclopropyl(NHR₃)] | 1 | H | — | — |
| O | OH | H | [C(O)-cyclopropyl(NHR₃)] | 1 | H | — | — |
| O | OH | H | [C(O)-cyclopropyl(NHR₃)] | 2 | H | — | — |
| O | OH | H | [C(O)-cyclopropyl(NHR₃)] | 3 | H | — | — |
| O | OH | H | [C(O)-cyclopropyl(NHR₃)] | 4 | H | — | — |
| $CH_2$ | OH | H | $C(O)CH(NH_2)R_4$ | — | — | H | — |
| $CH_2$ | OH | H | $C(O)CH(NH_2)R_4$ | — | — | Me | — |
| $CH_2$ | OH | H | $C(O)CH(NH_2)R_4$ | — | — | Et | — |
| $CH_2$ | OH | H | $C(O)CH(NH_2)R_4$ | — | — | i-Pr | — |
| $CH_2$ | OH | H | $C(O)CH(NH_2)R_4$ | — | — | s-Bu | — |
| O | H | H | $C(O)CH(NH_2)R_4$ | — | — | H | — |
| O | OH | H | $C(O)CH(NH_2)R_4$ | — | — | H | — |

TABLE 2

Mixed di-Esters of Formula (I)

| A | B | R₁ | R₂ | n | R₃ | R₄ | R₅ |
|---|---|---|---|---|---|---|---|
| $CH_2$ | OH | $C(O)R_5$ | [C(O)-cyclopropyl(NHR₃)] | 1 | H | — | Me |
| $CH_2$ | OH | $C(O)R_5$ | [C(O)-cyclopropyl(NHR₃)] | 1 | H | — | Et |
| $CH_2$ | OH | $C(O)R_5$ | [C(O)-cyclopropyl(NHR₃)] | 1 | H | — | n-Pr |

TABLE 2-continued
Mixed di-Esters of Formula (I)
| A | B | R₁ | R₂ | n | R₃ | R₄ | R₅ |
|---|---|---|---|---|---|---|---|
| CH₂ | OH | C(O)R₅ | 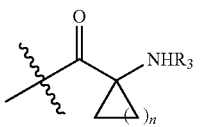 | 1 | H | — | t-Bu |
| CH₂ | OH | C(O)R₅ | 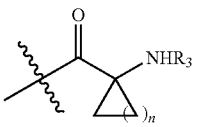 | 1 | Me | — | Me |
| CH₂ | OH | C(O)R₅ | 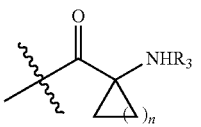 | 1 | Et | — | Me |
| CH₂ | OH | C(O)R₅ | 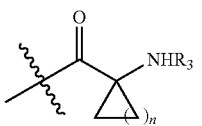 | 1 | i-Pr | — | Me |
| CH₂ | OH | C(O)R₅ | 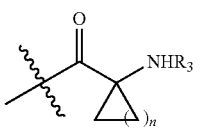 | 1 | s-Bu | — | Me |
| CH₂ | H | C(O)R₅ | 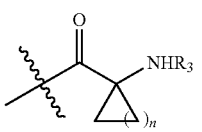 | 1 | H | — | Me |
| O | H | C(O)R₅ | 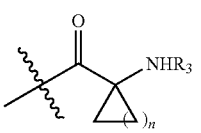 | 1 | H | — | Me |
| O | OH | C(O)R₅ | 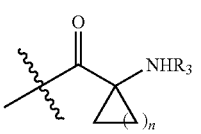 | 1 | H | — | Me |
| O | OH | C(O)R₅ | 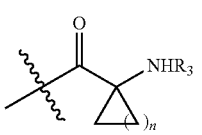 | 1 | H | — | i-Pr |
| O | OH | C(O)R₅ | 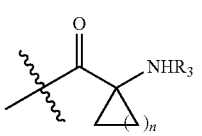 | 1 | H | — | n-Pr |
| CH₂ | H | C(O)R₅ | C(O)CH(NH₂)R₄ | — | — | Me | i-Pr |
| CH₂ | OH | C(O)R₅ | C(O)CH(NH₂)R₄ | — | — | Me | i-Pr |
| O | H | C(O)R₅ | C(O)CH(NH₂)R₄ | — | — | Me | i-Pr |
| O | OH | C(O)R₅ | C(O)CH(NH₂)R₄ | — | — | Me | i-Pr |

TABLE 2-continued

Mixed di-Esters of Formula (I)

| A | B | R$_1$ | R$_2$ | n | R$_3$ | R$_4$ | R$_5$ |
|---|---|---|---|---|---|---|---|
| CH$_2$ | H | [1-(NHR$_3$)cyclopropyl-C(O)-] | C(O)CH(NH$_2$)R$_4$ | 1 | H | — | i-Pr |
| CH$_2$ | OH | [1-(NHR$_3$)cyclopropyl-C(O)-] | C(O)CH(NH$_2$)R$_4$ | 1 | H | — | i-Pr |
| O | H | [1-(NHR$_3$)cyclopropyl-C(O)-] | C(O)CH(NH$_2$)R$_4$ | 1 | H | — | i-Pr |
| O | OH | [1-(NHR$_3$)cyclopropyl-C(O)-] | C(O)CH(NH$_2$)R$_4$ | 1 | H | — | i-Pr |

TABLE 3

Symmetrical di-Esters of Formula (I)

| A | B | R$_1$ | R$_2$ | n | R$_3$ | R$_4$ | R$_5$ |
|---|---|---|---|---|---|---|---|
| CH$_2$ | H | [1-(NHR$_3$)cyclopropyl-C(O)-] | [1-(NHR$_3$)cyclopropyl-C(O)-] | 1 | H | — | — |
| O | H | [1-(NHR$_3$)cyclopropyl-C(O)-] | [1-(NHR$_3$)cyclopropyl-C(O)-] | 1 | H | — | — |
| CH$_2$ | OH | [1-(NHR$_3$)cyclopropyl-C(O)-] | [1-(NHR$_3$)cyclopropyl-C(O)-] | 1 | H | — | — |
| CH$_2$ | OH | [1-(NHR$_3$)cyclopropyl-C(O)-] | [1-(NHR$_3$)cyclopropyl-C(O)-] | 1 | Me | — | — |
| CH$_2$ | OH | [1-(NHR$_3$)cyclopropyl-C(O)-] | [1-(NHR$_3$)cyclopropyl-C(O)-] | 1 | Et | — | — |
| CH$_2$ | OH | [1-(NHR$_3$)cyclopropyl-C(O)-] | [1-(NHR$_3$)cyclopropyl-C(O)-] | 1 | i-Pr | — | — |
| CH$_2$ | OH | [1-(NHR$_3$)cyclopropyl-C(O)-] | [1-(NHR$_3$)cyclopropyl-C(O)-] | 1 | s-Bu | — | — |
| CH$_2$ | OH | [1-(NHR$_3$)cyclopropyl-C(O)-] | [1-(NHR$_3$)cyclopropyl-C(O)-] | 1 | t-Bu | — | — |
| O | OH | [1-(NHR$_3$)cyclopropyl-C(O)-] | [1-(NHR$_3$)cyclopropyl-C(O)-] | 1 | H | — | — |
| O | OH | [1-(NHR$_3$)cyclopropyl-C(O)-] | [1-(NHR$_3$)cyclopropyl-C(O)-] | 1 | Me | — | — |
| O | OH | [1-(NHR$_3$)cyclopropyl-C(O)-] | [1-(NHR$_3$)cyclopropyl-C(O)-] | 1 | Et | — | — |
| O | OH | [1-(NHR$_3$)cyclopropyl-C(O)-] | [1-(NHR$_3$)cyclopropyl-C(O)-] | 1 | i-Pr | — | — |
| O | OH | [1-(NHR$_3$)cyclopropyl-C(O)-] | [1-(NHR$_3$)cyclopropyl-C(O)-] | 1 | s-Bu | — | — |

TABLE 3-continued

Symmetrical di-Esters of Formula (I)

| A | B | R₁ | R₂ | n | R₃ | R₄ | R₅ |
|---|---|---|---|---|---|---|---|
| O | OH | [structure: C(O)-cyclopropyl-NHR₃] | [structure: C(O)-cyclopropyl-NHR₃] | 1 | t-Bu | — | — |
| CH₂ | H | C(O)R₅ | C(O)R₅ | — | — | — | Me |
| CH₂ | OH | C(O)R₅ | C(O)R₅ | — | — | — | Me |
| O | H | C(O)R₅ | C(O)R₅ | — | — | — | Me |
| O | OH | C(O)R₅ | C(O)R₅ | — | — | — | Me |
| CH₂ | H | C(O)CH(NH₂)R₄ | C(O)CH(NH₂)R₄ | — | — | i-Pr | — |
| CH₂ | OH | C(O)CH(NH₂)R₄ | C(O)CH(NH₂)R₄ | — | — | i-Pr | — |
| O | H | C(O)CH(NH₂)R₄ | C(O)CH(NH₂)R₄ | — | — | i-Pr | — |
| O | H | C(O)CH(NH₂)R₄ | C(O)CH(NH₂)R₄ | — | — | i-Pr | — |

In Table 4 below, the substituent R' exemplifies an alkyl of 1-4 carbon atoms.

TABLE 4

Formula (II)

| n | R' |
|---|---|
| 1 | H |
| 1 | Me |
| 1 | Et |
| 1 | i-Pr |
| 1 | t-Bu |
| 2 | H |
| 2 | Me |
| 2 | Et |
| 2 | n-Pr |
| 2 | n-Bu |
| 3 | H |
| 3 | Me |
| 3 | Et |
| 3 | i-Pr |
| 3 | i-Bu |
| 4 | H |
| 4 | Me |
| 4 | Et |
| 4 | i-Pr |
| 4 | t-Bu |

As used herein, the below terms have the indicated meanings.

The term "alkyl of 1-4 carbon atoms" refers to a straight, branched or cyclic alkyl chain having from 1-4 carbon atoms, and includes methyl ("Me"), ethyl ("Et"), n-propyl ("n-Pr"), iso-propyl ("i-Pr"), cyclopropyl ("c-Pr"), n-butyl ("n-Bu"), iso-butyl ("i-Bu"), sec-butyl ("s-Bu"), tert-butyl ("t-Bu"), and the like. In likewise fashion, "alkyl of 1-5 carbon atoms" will encompass similar family members, including cyclopentyl ("c-Pent"), and the like. The term "alkoxy of 1-6 carbon atoms" refers to a straight, branched or cyclic alkyl chain attached via an oxygen atom linker, and includes methoxy ("MeO"), n-propoxy ("n-PrO"), tert-butoxy ("t-BuO"), cyclohexanoxy ("c-HexO"), and the like.

The naming of specific compounds listed herein conforms to nomenclature recommended by the International Union of Pure and Applied Chemistry (IUPAC), such naming being recognized by those skilled in the art.

As with any group of pharmaceutically active compounds, some groups are preferred in their end use application. In one aspect of the invention where a compound of Formula (I) encompasses A is CH₂, it is preferred that B is H, and R₁ is 1-aminocyclo-propylcarboxylate. It is more preferred that B is H, R₁ is 1-aminocyclopropylcarboxylate, and R₂ is H. In another aspect of the invention where a compound of Formula (I) encompasses A is O, it is preferred that B is OH, n is 1 and R₃ is H. It is more preferred that B is OH, n is 1, R₃ is H, and R₂ is C(O)Me or C(O)CH(NH₂)i-Pr.

The compounds useful in this invention may be in crystalline form or as a hydrate or in the form of a pharmaceutically acceptable salt. Examples of pharmaceutically acceptable salts of the compounds of Formulas (I) or (II) are acid addition salts formed with a pharmaceutically acceptable acid such as hydrochloric acid, sulfuric acid, phosphoric acid, maleic acid, fumaric acid, citric acid, tartaric acid, lactic acid, acetic acid, and the like. It would be recognized by one of ordinary skill in the art that one or more centers of chirality may be present in compounds of Formula (I), and such compounds may therefore exist as stereoisomers. While all enantiomers, diastereomers, and mixtures thereof, are contemplated within the present invention, preferred embodiments are single enantiomers and single diastereomers.

Compounds of Formula (II) have been prepared by processes known in the chemical art for the production of structurally analogous compounds. Such techniques are well known and appreciated in the art. See, for example, PCT publication No. WO2006/127217 A2.

More specifically, as illustrated in Scheme 1 below, acyclovir is combined with a compound of Formula A having an amino protecting group, under acylation reaction conditions, to result in ester formation. Well-known coupling reagents such as carbodiimides with or without the use of additives such as N-hydroxysuccinimide may be used to facilitate ester formation, and yield the compound of Formula B. The reaction may also be performed in the presence of a base such as triethylamine. The reaction is conveniently conducted in an inert aprotic solvent such as pyridine, methylene chloride, dimethylformamide and the like.

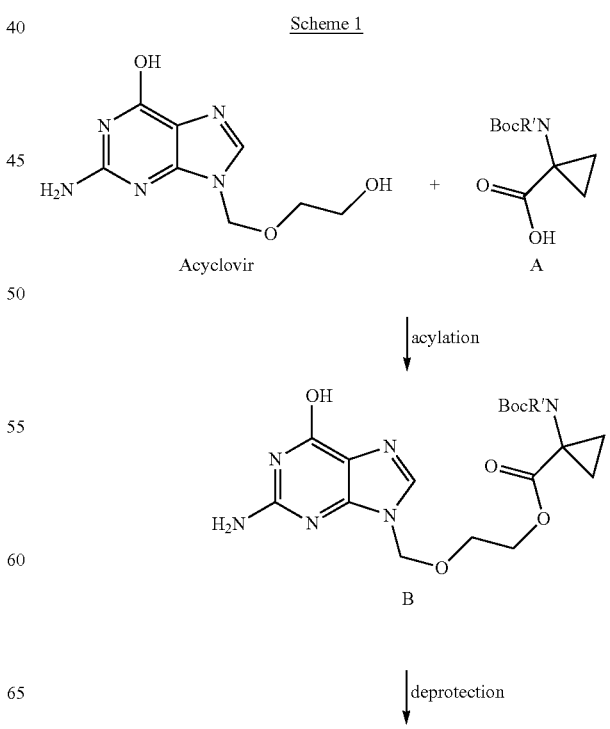

Scheme 1

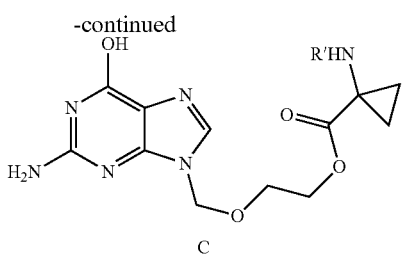

C

The compound of Formula B is treated with reagents suitable for removing the tert-Butyloxycarbonyl ("Boc") protecting group without adversely affecting the molecule. The conditions to remove such protecting groups are within the knowledge of the skilled artisan. In this case, the compound of Formula B is treated with trifluoroacetic acid in a suitable solvent such as methylene chloride to provide the desired compound of Formula C.

Compounds of Formula (I), or pharmaceutically acceptable salt thereof, are prepared by processes known in the chemical art for the production of structurally analogous compounds, such as those of Formula (II) described above. Such techniques are well known and appreciated in the art, and are illustrated in Scheme 2 below.

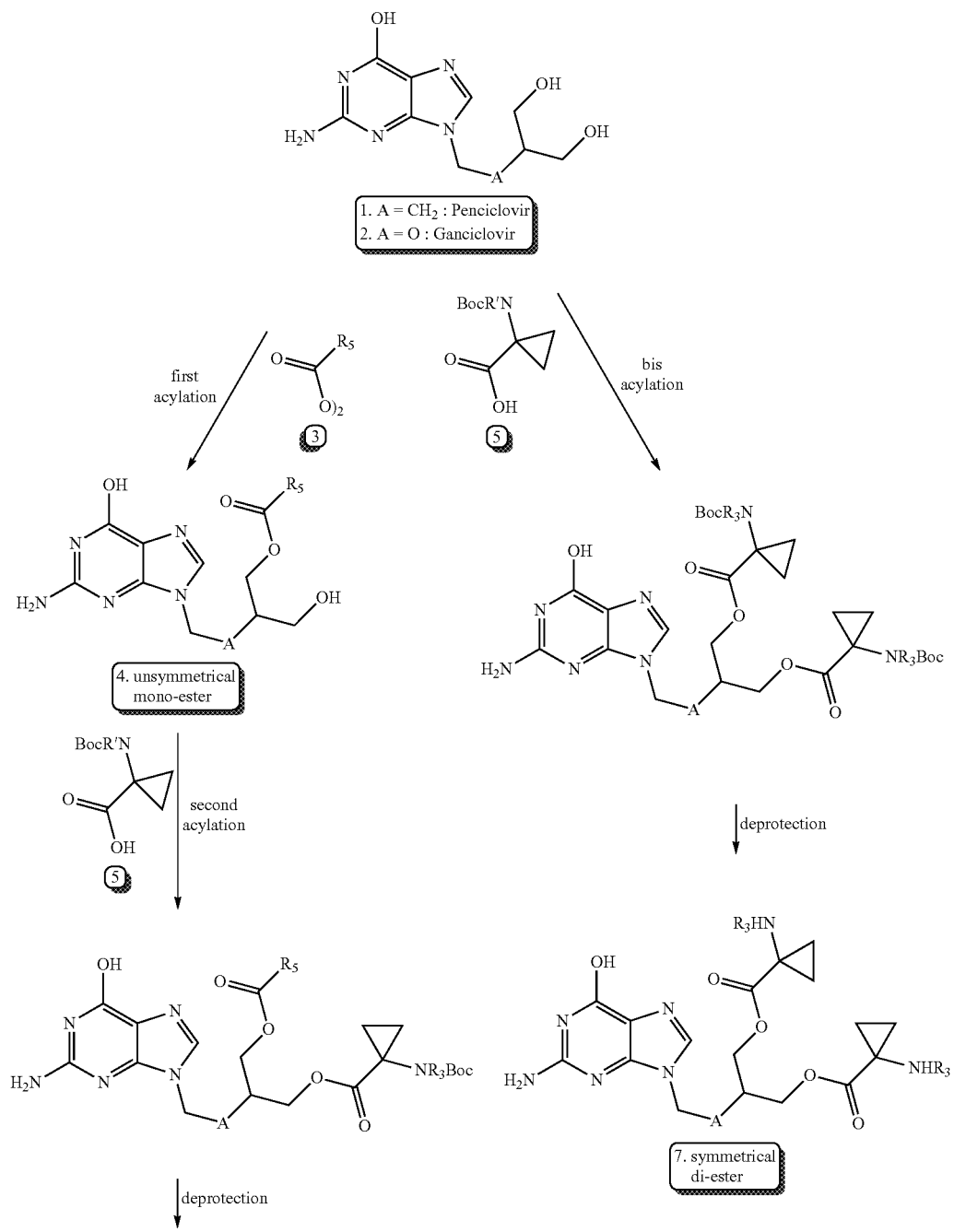

Scheme 2

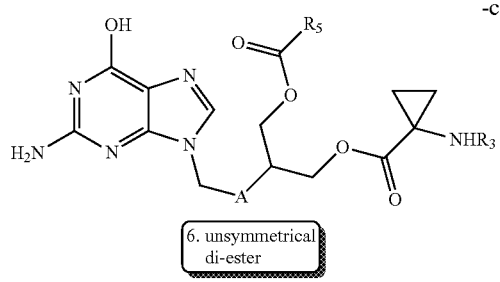

6. unsymmetrical di-ester

More specifically, Penciclovir (1, A=CH$_2$) or Ganciclovir (2, A=O) can be converted to the unsymmetrical mono-ester derivative by treating with an appropriate anhydride type 3, under acylation reaction conditions, to result in compound type 4. Treatment of 4 with N-protected amino-acid type 5, under acylation reaction conditions, would provide the unsymmetrical di-ester, which after removal of the nitrogen protecting group would afford the desired product 6. Alternatively, treatment of Penciclovir (1, A=CH$_2$) or Ganciclovir (2, A=O) with typically 3 equivalents of N-group protected amino-acid 5 under acylation reaction conditions, would yield the symmetrical diester 7, following removal of the nitrogen protecting group. Well-known coupling reagents such as carbodiimides with or without the use of additives such as N-hydroxysuccinimide may be used to facilitate ester formation. The reaction may also be performed in the presence of a base such as triethylamine. The reaction is conveniently conducted in an inert aprotic solvent such as pyridine, methylene chloride, dimethylformamide and the like. Control of the acylation conditions and choice of nitrogen protecting group are necessary to optimize the yield of the desired mono- or di-ester product, such variables being apparent to those skilled in the art, as are the conditions to remove protecting groups. Other starting materials, where "B" of Formula (I) is a moiety other than OH, may be used to obtain compounds useful in this invention.

In this example, reagents suitable for removing the tert-Butyloxycarbonyl ("Boc") protecting group without adversely affecting the molecule include trifluoroacetic acid in a suitable solvent such as methylene chloride. Synthetic routes to analogs bearing alternative substituents to the 4-hydroxyl group are well known in the art.

Compounds of Formulas (I) or (II), or pharmaceutically acceptable salt thereof, can be administered alone or in the form of a pharmaceutical composition, that is, combined with pharmaceutically acceptable carriers, diluents or excipients, the proportion and nature of which are determined by solubility and chemical properties, including stability of the compound selected, the chosen route of administration, and standard pharmaceutical practice, as discussed later.

Administration

It is recognized that one skilled in the art may affect a herpes virus infection by treating a patient presently infected with the virus and displaying symptoms or by prophylactically treating an infected patient at risk of a future symptom outbreak with an effective amount of the compound of Formulas (I) or (II), or pharmaceutically acceptable salt thereof. Thus, the terms "treatment" and "treating" are intended to refer to all processes wherein there may be a slowing, interrupting, arresting, controlling, or stopping of the progression of the herpes virus infection and/or symptoms thereof, but does not necessarily indicate a total elimination of all symptoms or infection, and is intended to include prophylactic treatment of such.

As used herein, the term "effective amount" of a compound of Formulas (I) or (II), or pharmaceutically acceptable salt thereof, refers to an amount, that is, the dosage which is effective in treating a herpes virus infection described herein. The attending diagnostician, as one skilled in the art, can readily determine an effective amount by the use of conventional techniques and by observing results obtained under analogous circumstances. In determining an effective amount, the dose of a compound of Formulas (I) or (II), a number of factors are considered by the attending diagnostician, including, but not limited to the compound of Formulas (I) or (II) to be administered; the co-administration of other antiviral agents, if used; the species of mammal; its size, age, and general health; the specific infecting virus; the degree of involvement or the severity of the infection; the response of the individual patient; the mode of administration; the bioavailability characteristics of the preparation administered; the dose regimen selected; the use of other concomitant medication; and other relevant circumstances.

For purposes of this invention, it is to be understood that administering a therapeutically effective amount of a compound of Formulas (I) or (II), or pharmaceutically acceptable salt thereof, encompasses a method wherein the compound of Formulas (I) or (II) itself is administered via a suitable pharmaceutical composition and the compound converts into acyclovir, penciclovir or ganciclovir upon being administered to subject in need thereof. For example, administering esters of penciclovir or ganciclovir shown in Tables 1-3 above result in plasma levels of penciclovir or ganciclovir, respectively, which are believed to be the active substances.

Generally, the compounds of Formulas (I) or (II), or pharmaceutically acceptable salt thereof, may be administered orally, rectally, vaginally, topically, intramuscularly (IM), intravenously (IV) or parenterally, but because of the ease of oral administration the oral route is generally employed. A composition which may be administered by the oral route to humans may be compounded in the form of an elixir, solution, suspension, syrup, tablet, caplet, capsule, or buccal formulation. When the composition is in the form of a tablet or caplet, any pharmaceutically acceptable excipient suitable for formulating such solid compositions may be used, for example magnesium stearate, starch, lactose, glucose, rice, flour and chalk. The composition may also be in the form of an ingestible capsule, for example of gelatin, to contain the compound. Suitable liquid pharmaceutical carriers include ethyl alcohol, glycerin, saline and water to which flavoring or coloring agents may be added. The compounds may also be presented with a sterile liquid carrier for injection. In general suitable pharmaceutical carriers and methods of preparation can be found in Remington's Pharmaceutical Sciences, 20th Edition.

In general, the type of pharmaceutical excipients and carriers are those that are used in the art for the compositions that already exist. For example, Famvir® is provided as a pharmaceutical composition which contains hydroxypropylcellulose, hydroxypropylmethylcellulose, lactose, magnesium stearate, polyethylene glycol, sodium starch glycolate and titanium dioxide. For acyclovir, Zovirax® capsules contain as an active ingredient acyclovir with inactive ingredients being cornstarch, lactose, magnesium stearate and sodium laurel sulfate, all of which are contained in a capsule shell of gelatin with FD&C Blue No. 2 and titanium dioxide. The tablets of Zovirax® at the 800 mg level contain as inactive ingredients FD&C Blue No. 2, magnesium stearate, microcrystalline cellulose, povidone, and sodium starch glycolate. Zovirax® is also available as a suspension which contains the active ingredient and the inactive ingredients methylparaben, propylparaben, carboxymethylcellulose sodium, flavor, glycerin, microcrystalline cellulose and sorbitol. Valtrex® capsules for oral administration contain valacyclovir hydrochloride and the inactive ingredients, carnauba wax, colloidal silicon dioxide, crospovidone, FD&C Blue No. 2 Lake, hydroxypropylmethylcellulose, magnesium stearate, microcrystalline cellulose, polyethylene glycol, Polysorbate®-80, povidone and titanium dioxide. Other compositions may be apparent to one of skill in the art upon reading this specification.

For intravenous infusion, the compounds may be provided as a sterile powder which is reconstituted with a sterile diluent. For these purposes, a sterile, lyophilized powder is prepared.

Because some subjects treated in accordance with this invention may have difficulty swallowing the number of pills required for effective treatment, it may be advantageous to provide a liquid-based composition that may be taken as a liquid elixir, syrup, solution or suspension. Such liquid-based formulations will generally be water-based and will comprise an active compound such as one shown in Tables 1-3 and optionally one or more of the following: an agent to aid in the solubilizing or suspending of the active compound, a flavoring agent, a preservative, a stabilizer, an antioxidant, a compatible co-solvent, an agent to provide acceptable sensory appeal, a pH adjuster, or a colorant. Other additives may be apparent to one of ordinary skill in the art upon reading this patent application. Solubilizing agents include polyethylene glycol, glycerin, monoethanolamine, propylene glycol and the like. Suspending agents include acacia, carboxymethylcellulose, polyvinyl alcohol, sodium lauryl sulfate, stearyl alcohol and the like. Flavoring agents include mint, peppermint, orange, lemon, lime, apple, cranberry, levulose, dextrose, saccharin, cherry, raspberry, and the like. Preservatives include methyl paraben, propyl paraben, butyl paraben, benzyl paraben, and the like. Stabilizers include bentonite, silica gel, glyceryl monostearate, magnesium hydroxide, cetyltrimethylammonium bromide, and the like. Antioxidants include citric acid, vitamin e, vitamin c, and the like. Compatible co-solvents include ethanol, glycerin, and the like. Suitable pH adjusters include ammonium chloride, calcium chloride, potassium bicarbonate, sodium carbonate, boric acid, potassium dihydrogen phosphate, and the like. Colorants include any approved by the FDA for oral ingestion such as FD&C yellow No. 6, FD&C blue No. 2, FD&C green No. 3, Citrus Red No. 2, and Ferric Oxide Red, as well as Annatto extract, beet powder, grape skin extract, turmeric and the like.

In some cases, it may be advantageous to provide a powder or granular mixture that is mixable with water to form a solution or suspension of the active compounds in water. Such a mixture may be provided in unit dosage packets or provided in a large container from which can be measured as a desired unit dosage. Such a granular or powder composition will be characterized in that it can be reconstituted, i.e., stirred or shaken with water, to give a therapeutically effective amount of the active compound to the person in need thereof by swallowing the liquid composition. Such a dry powder or granular formulation will comprise an active compound of Formulas (I) or (II), or pharmaceutically acceptable salt thereof, optionally along with at least one of the following: an agent to aid in dissolving or suspending the active compound, a flavoring agent, a preservative, a stabilizer, an antioxidant, a pH adjuster, or a colorant. Other additives may be apparent to one of ordinary skill in the pharmaceutical arts upon reading this application. In addition, the composition may be micronized or lyophilized to aid in the solution or suspension of the composition. Thus, another aspect of this invention is a powder or granular composition that comprises (a) a compound of Formulas (I) or (II) and (b) a pharmaceutically-acceptable excipient that aids in dissolving or suspending the compound of (a). A liquid composition comprises (a) a compound of Formulas (I) or (II) and (b) a liquid pharmaceutical excipient that aids in dissolving or suspending the compound.

Another composition that is part of this invention comprises a compound of Formulas (I) or (II), or pharmaceutically acceptable salt thereof, in the form of a suppository for rectal or vaginal administration. By administering rectally or vaginally, a patient who has difficulty swallowing pills can avoid the difficulty. A suppository, sometimes referred to as a pessary, provides systemic delivery of the compound across the rectal or vaginal mucosa through rapid disintegration and quick absorption. A suppository may be water insoluble or water soluble. Generally used bases for a water insoluble formulation include oil-soluble bases such as cocoa butter, sometimes referred to as theobroma oil, which is a pale yellow edible fat of the cocoa bean, and hydrogenated vegetable oil bases such as Witepsol®. Water soluble bases include polyethylene glycol (PEG), sometimes referred to as polyethylene oxide or PEO, or glycerin in combination with gelatin, an irreversibly hydrolyzed form of collagen.

Generally, very high doses of a compound of Formulas (I) or (II) are needed to provide a therapeutically-effective amount of the compounds. By administering the compounds of this invention at such levels, relief is seen of the signs or symptoms of a disease originating from the abnormal functioning of the SNS, as discussed hereinbefore. While any of the compounds encompassed within the generic formula of this invention can be used for treating the disease, an ester employing 1-aminocyclopropanecarboxylate is of particular interest. The rate and frequency of dosing depends on the extent of the autoimmune conditions, individual tolerance and the particular drug chosen for administration. Generally a therapeutically effective amount is a dosage that is very high relative to the levels effective for the treatment of conditions due to HSV such as HSV I or II or VZV. The therapeutically effective amount administered is sufficient to give the desired blood levels and ultimately the reduction of the signs or symptoms of the condition. The blood levels may vary from individual to individual. To achieve such a blood level, an amount administered on a daily basis will be equivalent to more than 150 mg, e.g., about at least 300, and preferably 300-400 mg famciclovir per kg body weight per day, although the amount administered depends on the activity and bioavailability of the particular compound administered, as well as how an individual responds to the amount administered. In some patients, the equivalent of 150 mg/kg/day famciclovir may be sufficient, while in others more than 300 mg/kg/day will be needed. Thus, for example, amounts such as those equivalent to 150, 160, 170, 180, 190, 200, 210, 220, 230, 240, 250, 260, 270, 280, 290, 300, 310, 320, 330, 340, 350, 360, 370, 380, 390, 400 mg/kg, or more, of famciclovir can be administered. In general the compounds are administered at times throughout a day to maintain a blood level that will continue to ameliorate the conditions, e.g. autoimmune or others, and provide relief to the individual from the signs or symptoms. Thus the dosing may be equal amounts provided 3 or up to 10 times a day depending on the individual and the compound chosen. Preferably the dosing is 3 to 8 times a day, particularly 4. Those skilled in the art of practicing drug dosage, delivery and pharmacokinetic analysis will, by reference to guidelines from texts such as 'Remington's Pharmaceutical Sciences' (17$^{th}$ Ed., Mack Publishing Co., 1985, Chapter 39, pp 762-772), 'Pharmacokinetics' (2$^{nd}$ Ed., Marcel Dekker, Inc., 1982) and 'The Pharmacological Basis of Therapeutics' (11$^{th}$ Ed., McGraw Hill, Inc., 2005), be able to calculate the appropriate quantities of compounds of Formulas (I) or (II), or pharmaceutically acceptable salt thereof, equivalent in activity to 150 mg/kg/day famciclovir.

In administering the compound of Formulas (I) or (II), or pharmaceutically acceptable salt thereof, it is administered at a rate that is equivalent in activity to famciclovir, about 150, particularly 300 to 400 mg/kg/day, e.g., about 15 to 40 g for a 100 kg person. Thus a 50 kg person (i.e. about 110 lbs) taking 300-400 mg/kg/day would take 15,000 to 20,000 mg famciclovir per day (50 kg×300 or 400 mg/day). Table 5 provides a list of daily equivalent minimum/maximum amounts that would be administered to subjects of various weights.

TABLE 5

| Weight - kg (lbs) | Dose mg/kg/day | Total Dose/day |
|---|---|---|
| 50 (110) | 150, 300-400 | 7500, 15,000-20,000 mg |
| 60 (132) | 150, 300-400 | 9000, 18,000-24,000 mg |
| 70 (154) | 150, 300-400 | 10,500, 21,000-28,000 mg |
| 80 (176) | 150, 300-400 | 12,000, 24,000-32,000 mg |
| 90 (198) | 150, 300-400 | 13,500, 27,000-36,000 mg |
| 100 (220) | 150, 300-400 | 15,000, 30,000-40,000 mg |

It will be appreciated that because of the use of increased dosage of the compounds useful in this invention, an oral pill or tablet will contain larger amounts of a drug compound of Formulas (I) or (II), or pharmaceutically acceptable salt thereof. Thus, part of this invention is a container holding a plurality of tablets or capsules, each of which contains 800 to 1200 mg, e.g., at least 1000 mg of the compound of Formulas (I) or (II), and wherein the container is associated with a label providing instructions to administer the compound to a subject having a herpes infection and a disease associated with reduced blood flow to a tissue or organ the compound at a level and time sufficient to reduce the signs or symptoms associated with the disease, as discussed herein.

In addition to administering an anti-viral compound of Formulas (I) or (II), or pharmaceutically acceptable salt thereof, in accordance with this invention, it is useful to also co-administer a compound that decreases the rate of renal excretion of the compound of Formulas (I) or (II). Such co-administration may be performed by separately administering each compound or by combining the two compounds together in a single composition which may take the form of a capsule, tablet, caplet, syrup elixir, suppository, and the like, as discussed hereinbefore. In general the two compounds are administered simultaneously for ease of tracking consumption, but they be administered at different times during the day, if desired. An example of a compound that acts to decrease the rate of renal excretion is probenecid, 4-(dipropylsulfamoyl)benzoic acid. The compound is available commercially by the trade name of BENURYL. The normal dosage is suggested to be 500 mg twice per day for a 100 kg person, but may vary from individual to individual. Thus the dosage may vary, for example, from 400 to 600 mg twice per day. If the anti-herpetic drug is administered four times per day, probenecid may be administered four times per day at the rate of 250 mg (e.g., a range of 200 to 300) each time for a 100 kg person. As an example, if a 100 kg person is prescribed 300 mg of a compound of Formulas (I) or (II) per kg per day with the dose to be administered in four equal doses every six hours, the person would also be administered a total of about 1000 mg of probenecid. If the two ingredients are combined in an appropriate formulation to provide a tablet containing the appropriate content, such as the equivalent of 1000 mg famciclovir, probenecid would be present at a level of about 33.33 mg (within a range of about 25 to about 40 mg). Thus the person would ingest 7.5 tablets of the combination product. It will be recognized that some individuals may take slightly more or slightly less or may have a slight variance in the number of tablets taken instead of taking seven and a half 1000 mg tablets and still maintain effective blood levels for this invention. For example, a person may have a four times daily schedule such as the following: 1. seven 1000 mg tablets, 2. eight 1000 mg tablets, 3. seven 1000 mg tablets, and 4. eight 1000 mg tablets. Such a regimen provides the equivalent of 30,000 mg famciclovir per day to a 100 kg person.

Thus, one can see another aspect of this invention, a composition that comprises an anti-viral compound as described hereinbefore, a compound that decreases the renal excretion of the anti-viral compound, and a pharmaceutically acceptable excipient. The composition may be in a dosage form to be orally ingestible, for example in the form of a tablet, caplet, capsule, or any other forms discussed herein. The level of the anti-herpetic is equivalent to famciclovir at 800 to 1200 mg, while the level of the compound that decreases renal excretion, when it is probenecid, is 25 to 40 mg. Alternatively, the oral composition may be in the form of a liquid for oral administration, which is prepared to give the required dosage to achieve the desired level of effectiveness. Again, assuming that the desired daily dosage is 300 mg/kg/day for a 100 kg person, that is 30,000 mg total, a liquid unit dosage is prepared for administration in four equal dosages of about 7500 mg famciclovir and about 250 mg probenecid. In such a case the composition would be a liquid composition that comprises the anti-herpetic, the renal excretion reducer, and a suitable, pharmaceutically-acceptable liquid to suspend or dissolve one or both compounds to allow for the administration to treat the targeted condition. Another alternative is to provide a dry powder or granular mixture that when mixed with water is suspended or dissolved to provide a liquid composition for easy oral administration. In any of the formulations in which famciclovir and probenecid are combined, the ratio on a weight/weight (w/w) basis may vary from about 25:1 to 50:1 generally about 30:1.

In the past, it was observed, that a patient that stopped increasing the dosage of the anti-herpes drugs at the threshold of pain rarely achieves the relief of the autoimmune signs or symptoms. Patients who exceed the pain threshold and take over 20 g per day (over 200 mg/kg/day) start experiencing a reduction in autoimmune symptoms for prolonged periods of time. The pain in such patients eventually disappears. Patients who take even higher doses, 30 g per day for a 100 kg subject (300 mg/kg) and higher, experience a continuous relief of at least 90% of all of their autoimmune signs or symptoms, including pain, as long as they continue taking the drug.

EXAMPLE

The following example is given to one of ordinary skill in the art as guidance in preparing compounds useful in the invention described in this application. This example is reproduced from Preparation 1 and Examples 1-2 of PCT Publication No. WO2006/127217 A2. By following the specific teachings of this example and the general guidance of the discussion of preparation of other compounds, those of skill in the art will be taught how to make the compounds explicitly, and implicitly described in this application.

Preparation of 1-tert-butoxycarbonylamino-cyclopropanecarboxylic acid 2-(2-amino-6-oxo-1,6-dihydro-purin-9-ylmethoxy)-ethyl ester

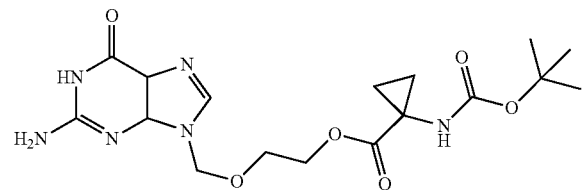 [SMILES: CC(C)(C)OC(=O)NC1(C(=O)OCCOCN2C=NC3C(=O)NC(N)=NC32)CC1]

Combine acyclovir (0.50 g, 2.22 mmol) with t-Boc-aminocyclopropyl carboxylic acid (0.58 g, 2.89 mmol), 1-ethyl-3-(3-dimethylaminopropyl)-carbodiimide (0.64 g, 3.33 mmol) and 4-dimethylaminopyridine (0.05 g, 0.36 mmol) in dry N,N-dimethylformamide (3 mL). Add triethylamine (0.31 g, 3.11 mmol) and stir the resulting suspension at room temperature under nitrogen overnight. Cool to 0° C. and add 10 mL of a 0.3 M solution of hydrochloric acid to precipitate a white solid. Collect by vacuum filtration and wash with ether. The resulting solid is recrystallized from isopropanol to give product as a white solid.

Yield: 93.7% MS (LC-MS): 409.3 (M+1). MS (LC-MS): 407.3 (M−1)

$^1$HNMR (d6-DMSO): δ 0.97 (s 2H); 1.23-1.24 (d, 2H); 1.33 (s, 9H); 3.60 (s, 2H); 4.07 (s, 2H); 5.32 (s, 2H); 6.50 (s, 2H); 7.50 (s, 1H); 7.78 (s, 1H); 10.65 (s, 1H)

Preparation of 1-amino-cyclopropanecarboxylic acid 2-(2-amino-6-oxo-1,6-dihydro-purin-9-ylmethoxy)-ethyl ester trifluoroacetic acid salt

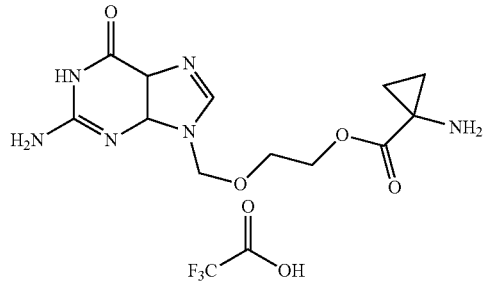

Suspend 1-tert-butoxycarbonylamino-cyclopropanecarboxylic acid 2-(2-amino-6-oxo-1,6-dihydro-purin-9-yl- methoxy)-ethyl ester (0.20 g, 0.49 mmol) in methylene chloride (2 mL) and stir at room temperature. Add trifluoroacetic acid (2 mL) dropwise and continue stirring. The suspension dissolves to give clear solution. Concentrate to dryness under vacuum. Triturate with ethyl acetate several times to isolate a white solid. Yield: 67.7% MS (ES+): 309.2 (M+1) MS (ES−): 307.2 (M−1)

$^1$HNMR (d6-DMSO): δ 0.84-1.30 (m, 4H); 3.65 (t, 2H); 4.21 (t, 2H); 5.33 (s, 2H); 6.49 (s, 2H); 7.82 (s, 1H); 8.64 (s, 2H); 10.66 (s, 1H)

Preparation of 1-amino-cyclopropanecarboxylic acid 2-(2-amino-6-oxo-1,6-dihydro-purin-9-ylmethoxy)-ethyl ester

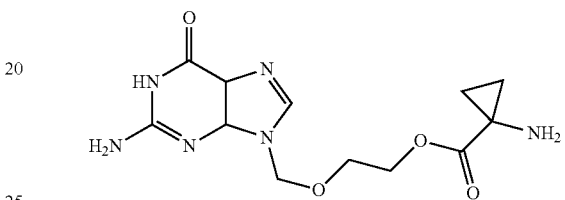

Dissolve 1-amino-cyclopropanecarboxylic acid 2-(2-amino-6-oxo-1,6-dihydropurin-9-ylmethoxy)-ethyl ester trifluoroacetic acid salt (0.02 g, 0.05 mmol) in 1 mL methanol. Apply this solution to a 1 g Varian Mega Bond Elute® SCX column (Varian Part#170532) pre-washed several times with methanol. Wash the column with 10 mL of methanol then elute the compound with 15 mL of a 2 M solution of ammonia in methanol. Concentrate in vacuo to obtain the desired free base as a white solid.

MS (ES+): 309.2 (M+1)

$^1$HNMR (d6-DMSO): δ 0.78 (q, 2H); 1.01 (q, 2H); 2.18 (s, 2H); 3.62 (m, 2H); 4.06 (m, 2H); 5.32 (s, 2H); 6.47 (s, 2H); 7.79 (s, 1H)

Hydrolytic stability of valacyclovir and 1-aminocyclopropanecarboxylic acid 2-(2-amino-6-oxo-1,6-dihydro-purin-9-ylmethoxy)-ethyl ester trifluoroacetic acid salt Test samples of valacyclovir and 1-amino-cyclopropanecarboxylic acid 2-(2-amino-6-oxo-1,6-dihydro-purin-9-ylmethoxy)-ethyl ester trifluoroacetic acid salt are dissolved in buffered solutions of known pH at a concentration of 100 µg/mL. Compound samples are prepared in 0.1 N hydrochloric acid for pH 1 and phosphate based buffer for pH 2, 4, 6, 8 and 10. Stability is conveniently assessed using a semi-automated HPLC technique. Compound samples are loaded onto an HPLC autosampler incubated at 40° C. Samples are repeatedly injected on the HPLC at specific time intervals. The peak area of the compound samples are monitored by UV detection.

HPLC Method

The HPLC system consisted of an Agilent® 1100 autoinjector, pump, degasser and UV detector. A Waters® Atlantis dC-18 column (3 micron, 150×4.6 mm I.D.) is used to separate the degradation products from the compound sample. An isocratic reversed-phase system using ultraviolet detection is used to monitor the peak areas of the compound sample over a 24 hour period. The mobile phase composition is 5% acetonitrile and 95% water with 0.1% trifluoroacetic acid added to the mixture. The flow rate is 1.5 mL/min. The column temperature is 30° C. and the injection volume was 10 μL. The UV detector is set at 256 nm and the run time was 9 minutes. Time points are analyzed every 2 hours for each buffer while being incubated at 40° C. by the thermostat controlled autosampler.

Half-Life Calculation

The peak area of the compound sample is monitored over a 24 hour period at 2 hour intervals. The peak area of the compound sample is plotted versus time for each of the buffers tested. A first order calculation is used to determine the rate constant for each buffer based on the loss of peak area over time. The half-life, in hours, is calculated by dividing 0.693 by the rate constant (k). t½ (hr)=0.693/k. The results are presented in Table 6.

TABLE 6

| | $t_{1/2}$ (hr) at 40° C. | | | | | |
|---|---|---|---|---|---|---|
| Sample | pH = 1 | pH = 2 | pH = 4 | pH = 6 | pH = 8 | pH = 10 |
| valacyclovir | >300 | >300 | >300 | 69.7 | 7.8 | 6.8 |
| Example | >300 | >300 | >300 | >300 | 90.1 | 23.8 |

Further aspects of this invention may be apparent to those of skill in the art upon further contemplation of this disclosure.

What is claimed is:

1. A compound of the formula 1.

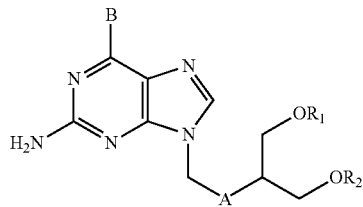

wherein A is $CH_2$ [or O];
B is H, Cl, alkoxy of 1-6 carbon atoms, phenoxy, phenylalkoxy where alkoxy is 1-6 carbon atoms, $NH_2$, OH or SH;
$R_1$ is
2.

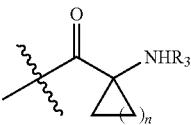

wherein n is 1 and $R_3$ is H or alkyl of 1-4 carbon atoms; and
$R_2$ is independently H, $C(O)R_5$ where $R_5$ is alkyl of 1-5 carbon atoms, $C(O)CH(NH_2)R_4$ where $R_4$ is H or alkyl of 1-4 carbon atoms, proline, hydroxyproline, or
3.

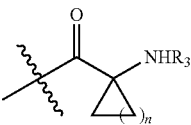

wherein n and $R_3$ are as defined above,
or a pharmaceutically acceptable salt thereof.

2. A compound of claim 1, wherein A is $CH_2$ and B is H or OH.

3. A compound of claim 2, wherein B is H, $R_2$ is the same as $R_1$, and $R_3$ is H.

4. A compound of claim 1, wherein $R_2$ is H; $C(O)R_5$ where $R_5$ is Me or Et; or $C(O)CH(NH_2)R_4$ where $R_4$ is Me, Et, i-Pr or s-Bu; or $R_1$.

5. A compound of claim 1, wherein A is $CH_2$, B is H, and $R_2$ is H, C(O)Me or C(O)CH(NH_2)i-Pr, or $R_1$.

* * * * *